United States Patent [19]
Holloman et al.

[11] Patent Number: 5,945,339
[45] Date of Patent: Aug. 31, 1999

[54] METHODS TO PROMOTE HOMOLOGOUS RECOMBINATION IN EUKARYOTIC CELLS AND ORGANISMS

[75] Inventors: William K. Holloman, Yorktown Heights, N.Y.; Eric B. Kmiec, Malvern, Pa.

[73] Assignees: Cornell Research Foundation, Inc., Ithaca, N.Y.; Thomas Jefferson University, Philadelphia, Pa.

[21] Appl. No.: 09/114,637

[22] Filed: Jul. 13, 1998

Related U.S. Application Data

[63] Continuation of application No. 08/373,134, Jan. 17, 1995, Pat. No. 5,780,296.
[51] Int. Cl.$^6$ ..................................................... C12N 15/64
[52] U.S. Cl. .......................... 435/477; 435/483; 435/484
[58] Field of Search .................................. 435/477, 483, 435/484

[56] References Cited

U.S. PATENT DOCUMENTS

| | | | |
|---|---|---|---|
| 4,873,191 | 10/1989 | Wagner et al. | 435/317.1 |
| 4,950,599 | 8/1990 | Bertling et al. | 435/456 |
| 5,139,941 | 8/1992 | Muzyczka et al. | 435/456 |
| 5,354,678 | 10/1994 | Lebkowski et al. | 435/463 |

FOREIGN PATENT DOCUMENTS

| | | |
|---|---|---|
| WO 90/09441 | 8/1990 | WIPO . |
| WO 92/07945 | 5/1992 | WIPO . |
| WO 93/22443 | 11/1993 | WIPO . |
| WO 94/04032 | 3/1994 | WIPO . |
| WO 94/08026 | 4/1994 | WIPO . |
| WO 94/10322 | 5/1994 | WIPO . |

OTHER PUBLICATIONS

Thomas, "Recombination of DNA Molecules", Prog Nuc Acid Res Mol Biol. 5:315 (1966).
Holliday et al. "Altered Recombination Frequencies in Radiation Sensitive Strains of Ustilago", Mutation Res 4:275–288 (1967).
Sande et al.,"Phosphorylation of N–Protected Deoxyoligonucleotides by T4 Polynucleotide Kinase", Biochem 12:5056–5062 (1973).
Holliday et al., "Genetic Characterization of rec–1, a Mutant of *Ustilago maydis* Defective in Repair and recombination", Genet Res 27:413–453 (1976).
van Weezenbeek et al., "Nucleotide Sequence of the Filamentous Bacteriophage M13 DNA Genome Compairson with Phage fd", Gene 11:129 (1980).
Doolittle, "Similar Amino Acid Sequences: Chance or Common Ancestry?", Science 241:149 (1981).
Bianchi et al., "Synapsis and the Formation of Paranemic Joints by *E. coli* RecA Protein", Cell 34:931 (1983).
Kmiec and Holloman, "Heteroduplex Formation and Polarity During Strand Transfer Promoted by Ustiligo Rec1 Protein", Cell 33:857–864 (1983).

Bradley et al., "Formation of Germ–line Chimaeras from Embryo–Derived Teratocarinoma Cell Lines", Nature 309:255–256 (1984).
Kmiec and Holloman, "Synapsis Promoted by Ustiligo Rec 1 Protein", Cell 36:593–598 (1984).
Kmiec and Holloman, "Homologous Pairing of DNA Molecules by Ustiligo Rec 1 Protein is Promoted by Sequences of Z–DNA", Cell 44:545–554 (1986).
Studier and Moffatt, "Use of Bacteriophage T7 RNA Polymerase to Direct Selective High–level Expression of Cloned Genes", J Mol Biol 189:113–130 (1986).
Thomas and Capecchi, "Site–Directed Mutagenesis by Gene Targeting in Mouse Embryo–Derived Sterm Cells", Cell 51:503–512 (1987).
Moerschel et al., "Transformation of Yeast with Synthetic Oligonucleotides", PNAS USA 85:524 (1988).
Pearson et al., "Improved Tools for Biological Sequence Comparison"PNAS USA 85:2444–2448 (1988).
Brinster et al., "Targeted Correction of a Major Histocompatibility Class II Eα Gene by DNA Microinjected into Mouse Eggs", PNAS USA 86:7087–7091 (1989).
Capecchi, "Altering the Genome by Homologous Recombination", Science 244:1288–1292 (1989).
Chisaki and Capecchi,"Regionally Restricted Developmental Defects Results from targeted Disruption of the Mouse Homeobox Gene hox–1.5", Nature 350:473–479 (1989).
Ho et al., "Site–directed Mutagenesis by Overlap Extension Using the Polymerase Chain Reaction", Gene 77:51–59 (1989).
Shenoy et al., "Purified Maturation Promoting Factor Phosphorylates pp60$^{c-src}$ at the Sites Phosphorylated during Fibroblast Mitosis", Cell 57–763–774 (1989).
Tsukuda et al., "Isolation of the REC1 Gene Controlling Recombination in *Ustiligo maydis*", Gene 85:335–341 (1989).

(List continued on next page.)

*Primary Examiner*—James Ketter
*Attorney, Agent, or Firm*—Daniel Hansburg

[57] ABSTRACT

The invention concerns genes encoding recombinases that can be used to promote homologous recombination in eukaryotic cells. The application teaches methods by which a recombinase of one species can be used to isolate a homologous recombinase of a different species and methods to identify the isolated homologs. Recombinases from *Ustilago maydis*, *Saccharomyces cerevisiae* and humans are specifically included in the invention.

The invention encompasses the method of producing an isolated recombinase protein in a prokaryotic cell and recovering the product in an active form. The invention also encompasses a genetically engineered gene which encodes a non-naturally occurring recombinase that causes a greater rate of recombination than does the naturally occurring recombinase. The invention further encompasses the use of recombinase proteins and of recombinase genes to promote homologous recombination, including recombination between a host cell genome and a chimeric oligonucleotide, i.e., an oligonucleotide having both RNA and DNA bases.

6 Claims, 10 Drawing Sheets

OTHER PUBLICATIONS

Bauchwitz and Holloman, "Isolation of the REC2 Gene Controlling Recombination in *Ustiligo maydis*", Gene 96:285–288 (1990).

Lewin, "Driving the Cell Cycle: M Phase Kinase, Its Partners and Substrates", Cell 61:743–752 (1990).

Pearson, "Rapid and Sensitive Sequence Comparison with FASTP and FASTA", Methods in Enzymology, 183:63–98 (1990).

Fotheringham and Holloman, "Extrachromosomal Recombination Is Deranged in the rec2 Mutant of *ustiligo maydis*", Genetics 129:1053–1060 (1991).

Hunger, "The t(1;19)(q23;p13) Results in Consistent Fusion of E2A and PB1X1 Coding Sequences in Acute Lymphoblastic Leukemias",Blood 77:687–693 (1991).

Reed, "The Role of p34 Kinases in the G1 to S–Phase Transition", Ann Rev Cell Biol 8:529–561 (1992).

Shenoy et al., "Role of p34$^{cdc2}$–mediated Phosphorylations in Two–step Activation of pp60$^{c-src}$ During Mitosis", PNAS USA 89:7237–7241 (1992).

Rao and Radding, "Homologous Recognition Promoted by RecA Protein Via non–Watson–Crick Bonds Between Identical DNA Strands", PNAS USA 90:6646–6650 (1993).

Crystal et al., "Administration of an Adenovirus Containing the Human CFTR cDNA to the Respiratory Tract of Individuals with Cystic Fibrosis", Nature Genetics 8:42–51 (1994).

Kaplitt et al., "Long–term Gene Expression and Phenotypic Correction Using Adeno–Associated Virus Vectors in Mammalian Brain", Nature Genetics 8:148–154 (1994).

Kmiec and Holloman, "DNA Strand Exchange in the Absence of Homologous Pairing", J Biol Chem 269:10163–10168 (1994).

Pines, "Ubiquitin With Everything", Nature 371:742–743 (1994).

Rubin et al., "Structure of REC2, a Recombinatorial Repair Gene of *Ustilago maydis*, and Its Function in Homologous Recombination between Plasmid and Chromosomal Sequences", Mol Cell Biol 14:6287–6296 (1994).

Kmiec and Holloman, "ATP Dependent DNA Renaturation and DNA–dependent ATPase Reactions Catalyzed by the *Ustiligo maydis* Homologous Pairing Protein", Eur J Bioch 219:865–875 (1994).

```
-175                                                                  AATATTCACGATTCTGATGTGGAAGCGTAAGGAGAAGCAGATTAGGTGCTGGTAGGAGCACCTCAACA
                                                                           SSPI
-107 AGCTAGCGCCTTGTCGTGCTCATCCCAGTCTTCCACAGCCCCAACCATCGTAGCGGCTGCGCATCGCCCAGAATGGTTGCGACTCACAGTTTGCACGTGCTAAATC

1 ATGACTGGCATCGCGATCGCGATGTTGGCTGCATTTGAAACGCATCAAGGCGTCGTGTGAGCGAAAGCTCTTCAGTACGACGAGATCCTCCTCAGCCCACCG
   1  M  T  G  I  A  I  A  D  V  G  C  I  S  K  R  I  K  A  C  C  R  R  A  K  L  F  S  T  D  E  I  L  L  S  P  P
                                                NLS

109 CAGCAATTGGCACACGTGTTGCGCATATCCCAAGCAGATGCCGATCTGCTTCTTCTCCAAGTGGCACTGCTCCCATCTCGGTACTGATGCGCTC
  37  Q  Q  L  A  H  V  L  R  I  S  Q  A  D  L  L  L  Q  V  A  T  A  S  A  P  P  P  I  S  V  L  D  A  L

217 AATGGCAAGCTTCCTGCTACCAACCTGGACCAGAACTTCTTTGACGCCGTCGCAGCAGCAGACGATGATGAGGACAATGATGAGGACGACGATGACAAAGCCGATTCC
  73  N  G  K  L  P  A  T  N  L  D  Q  N  F  F  D  A  V  A  A  A  D  D  D  D  N  D  D  D  D  D  K  A  D  S
                                                             CHROMATIN BINDING MOTIF

325 GGTTCGGCCGACGCTTCAGACGACGATGATCAACGAGGCCAAGGTTTGCCATCGTCTTGCATCGTCTTGCCCCAACACAGGGTACGATGGCAAC
 109  G  S  A  D  A  S  D  T  S  D  A  D  D  D  Q  H  L  N  D  A  R  F  A  S  S  C  I  V  P  P  T  Q  G  Y  D  G  N

433 TTTCCCGGGCACAATGCTTGTCTACGATTCCGACGCCGGCTCGGACAGTGATGCCGCGAGTAGCATCGACGAAGATATCGAGCTACCGTCCACC
 145  F  P  G  A  Q  C  F  V  Y  D  S  D  A  G  S  D  S  D  A  R  S  S  I  D  A  V  M  H  E  D  I  E  L  P  S  T

541 TTTTGCCGTCCACAAACACCACAAACCCGATGTTGCCCGTGACGAGCATCATGATGGGTATCTTTGCGATCCCAAAGTTGACCACGCCCTCGGTCGCCAGAGACGTC
 181  F  C  R  P  Q  T  P  Q  T  H  D  V  A  R  D  E  H  H  D  G  Y  L  C  D  P  K  V  D  H  A  S  V  A  R  D  V

649 TTATCGCTCGGACGCCAAGCAGCTGACGACGTATTCTCAAGGCGCTCCGACGAGCTGCTAGGCGGTGGGTGCGTTCCGGTGCTGCTCACCGAGCTCGTCGGTGAA
 217  L  S  L  G  R  Q  R  H  V  F  S  S  G  S  R  E  L  D  D  L  L  G  G  G  V  R  S  A  V  L  T  E  L  V  G  E
```

FIG. 1A

```
 757 AGGGGCTCTGGTAAGACCCAGATGGCTATCCAAGTTTGCACTTATGCGCTCTCGGCTTGGTTCCGCTGAGCCAAGCTGACGATCACGACAAGGGCAACAACACATTT
 253 S  G  S  G  K  T  Q  M  A  I  Q  V  C  T  Y  A  A  L  G  L  V  P  L  S  Q  A  D  D  H  D  K  G  N  N  T  F
         MOTIF A
 865 CAATCCAGGACTTTCGTACGAGACCCGATACACGCTTCGACCAAAGACGACACACTAAGGACATTCTGCAGAGCTACGGCATGGAGCCCTCGATTGGATCTCACCGC
 289 Q  S  R  T  F  V  R  D  P  I  H  A  S  T  K  D  D  T  L  S  D  I  L  Q  S  Y  G  M  E  P  S  I  G  S  H  R

973 GGTATGGGCGCGTGCTACATCACATCTGGTGGGGAGCGCGCAGCTCTGAACCGAGCTCTGGAACTTGCAAGCTTTGCTATCAACGAACGCTTTGATCGC
 325 G  M  G  A  C  Y  I  T  S  G  G  E  R  A  A  H  S  I  V  N  R  A  L  E  L  A  S  F  A  I  N  E  R  F  D  R

1081 GTCTATCCGGTCTGCGATCCTACACAAAGCTCGCAGGACGCCGATGGGCGCCCGACGCATTGCTGGCCAAGGCACAGCAGCTTGGTCGTGACAAGGCTTGCCAAC
 361 V  Y  P  V  C  D  P  T  Q  S  S  Q  D  A  D  G  R  R  G  A  L  L  A  K  A  Q  Q  L  G  R  R  Q  A  L  A  N

1189 TTGCACATAGCCTGCGTCGATGTCGAGGCATTGGAGCATGCTCTCAAGTACAGTTTGCCTGGCTTGATTCGTCGATTGTGGTCGAGTAAGCGTCAGTCGGGCGTA
 397 L  H  I  A  C  V  A  D  V  E  A  L  E  H  A  L  K  Y  S  L  P  G  L  I  R  R  L  W  S  S  K  R  Q  S  G  V

1297 TCGGCGAGATTGGCGTTGTGGTAGACAATCTTCCAGGCTTTTCCAGCAAGATCAAGGGGCAGGCGGATATCGACTCGCTCTTCCAAGCTCAAAGATGCTA
 433 S  R  E  I  G  V  V  V  D  N  L  P  A  L  F  Q  Q  D  Q  A  A  A  S  D  I  D  S  L  F  Q  R  S  K  M  L
                    MOTIF B

1405 GTCGAGATCGCGGATGCGCTCAAGCGTATCAGTGCTGTATCAGTGCTGTATACAATGGCGTAGAGGCGTAGAGGCGGTAGAGGCGGTAGGTGCGAACCACGTCAGC
 469 V  E  I  A  D  A  L  K  R  I  S  A  V  Q  W  R  G  A  S  D  C  G  S  S  A  G  R  A  V  L  V  L  N  H  V  S

1513 GATGCGTTTGGAATCGACAAGCAGATTGCACGGCGCTTCGTATTCGACTCGGCGCATCGGCTCTCATTTTGCAGCAACGATCCTGGCACATCA
 505 D  A  F  G  I  D  K  Q  I  A  R  R  F  V  F  D  S  A  H  R  I  R  T  R  R  S  H  F  A  R  N  D  P  G  T  S

1621 AGTCAAGGCGCCAACCTCGGCACTGGCAGCATTCAGCGGTGGCACTGGATCGGGTTACCGACCGCGTTACCAGAGACTGCGTTCACCAGCGGGCTGCTC
 541 S  Q  A  P  T  S  A  F  S  G  G  T  G  S  A  L  P  D  Q  P  L  A  M  D  V  A  S  Q  T  A  F  T  S  G  L  L
```

2809 TGGTAGCGTCCGATTTGATCGTTTCGCTGGCGGCCAATTTGGTGAAGCCTGCAGCATGGTCTTCGTCGGCGAACAGCAGATCCACGTCTTGCGTCT

2917 GCGTCGCCGAGCTGGGCGTGAGCAGCAACGCAACAGCGCTGCGAGCAATGTTGGCAACACGCTCACATTCGGCGCTCGAGCGCATGGCCGATGAATTCACCAACAAGC

3025 TCGCAA

73 N G K L P A T N L D Q N F F D A V A A A D D D D D D N D D D D D K A D S
                              TRP 1
109 G S A D A S D T S D A D D Q H L N D A R F A S S C I V P P T Q G Y D G N
                                          N-TERM 1
145 F P G A Q C F V Y D S D A G S D S D A R S S I D A V M H E D I E L P S T
                  N-TERM 2
181 F C R P Q T P Q T H D V A R D E H H D G Y L C D P K V D H A S V A R D V

217 L S L G R Q R H V F S S G S R E L D D L L G G G V R S A V L T E L V G E

253 S G S G K T Q M A I Q V C T Y A A L G L V P L S Q A D D H D K G N N T F

289 Q S R T F V R D P I H A S T K D D T L S D I L Q S Y G M E P S I G S H R

325 G M G A C Y I T S G G E R A A H S I V N R A L E L A S F A I N E R F D R
                                    TRP 3
361 V Y P V C D P T Q S S Q D A D G R R D A L L A K A Q Q L G R R Q A L A N

397 L H I A C V A D V E A L E H A L K Y S L P G L I R R L W S S K R Q S G V

433 S R E I G V V V V D N L P A L F Q Q D Q A A A S D I D S L F Q R S K M L

469 V E I A D A L K R I S A V Q W R G A S D C G S S A G R A V L V L N H V S

505 D A F G I D K Q I A R R F V F D S A H R I R T R R S H F A R N D P G T S
                              TRP 2
541 S Q A P T S A F S G G T G S A L P D Q P L A M D V A S Q T A F T S G L L

577 A S I A P T L A E A V G A R E L D S A C A S N D V P L R T L E A R T A Q

613 L G Q T W S N L I N V R V F L S K T R A R I C M R D D Q A P A C E P V R
                              TRP 4
649 Q N T N Q R G T A S K S L M N T V R K A A V V I N P F G A T M L D V G V

685 D K S A L R Q L R F V I T P R K A V H V L N A Y P S T V M H A M H A T A
                                                  TRP 5
721 D S T P A P E S Q Q Q Q R A A E R H P A E Q E D A D Q D L F G E A L Q E

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 3206 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 177..2520

(xi) SEQUENCE DESCRIPTION: SEQ ID NO:1:

```
AATATTCACG ATTCTGATGT GGAAGCGTAA GGAGAAGCAG ATTAGGTGCT GGTAGGAGCA        60

CCTCAACAAG CTAGCCGCCT TGTCGTGCTC ATCCCAGTCT TCCACAGCCC CAACCATCGT       120
```

```
AGCGGCTGCG CATCGCCACG AATGGTTGCG ACTCACAGCT TTGCACGTGC TAAATC                    176

ATG ACT GGC ATC GCG ATC GCC GAT GTT GGC TGC ATT TCG AAA CGC ATC                 224
Met Thr Gly Ile Ala Ile Ala Asp Val Gly Cys Ile Ser Lys Arg Ile
 1           5                   10                  15

AAG GCG TGC TGT CGT CGA GCA AAG CTC TTC AGT ACC GAC GAG ATC CTC                 272
Lys Ala Cys Cys Arg Arg Ala Lys Leu Phe Ser Thr Asp Glu Ile Leu
            20                  25                  30

CTC AGC CCA CCG CAG CAA TTG GCA CAC GTG TTG CGC ATA TCC CAA GCA                 320
Leu Ser Pro Pro Gln Gln Leu Ala His Val Leu Arg Ile Ser Gln Ala
         35                  40                  45

GAT GCC GAT CTG CTT CTT CTC CAA GTG GCC ACG GCA TCT GCT CCA CCT                 368
Asp Ala Asp Leu Leu Leu Leu Gln Val Ala Thr Ala Ser Ala Pro Pro
     50                  55                  60

CCC ATC TCG GTA CTC GAT GCG CTC AAT GGC AAG CTT CCT GCT ACC AAC                 416
Pro Ile Ser Val Leu Asp Ala Leu Asn Gly Lys Leu Pro Ala Thr Asn
 65                  70                  75                  80

CTG GAC CAG AAC TTC TTT GAC GCC GTC GCA GCT GCT GAC GAT GAC GAC                 464
Leu Asp Gln Asn Phe Phe Asp Ala Val Ala Ala Ala Asp Asp Asp Asp
                 85                  90                  95

GAC GAC AAT GAT GAT GAC GAT GAC AAA GCC GAT TCC GGT TCG GCC GAC                 512
Asp Asp Asn Asp Asp Asp Asp Asp Lys Ala Asp Ser Gly Ser Ala Asp
             100                 105                 110

GCT TCA GAC ACG AGC GAT GCG GAT GAT CAA CAT CTC AAC GAC GCA AGG                 560
Ala Ser Asp Thr Ser Asp Ala Asp Asp Gln His Leu Asn Asp Ala Arg
         115                 120                 125

TTT GCA TCG TCT TGC ATC GTG CCC CCA ACA CAG GGG TAC GAT GGC AAC                 608
Phe Ala Ser Ser Cys Ile Val Pro Pro Thr Gln Gly Tyr Asp Gly Asn
     130                 135                 140

TTT CCC GGC GCA CAA TGC TTT GTC TAC GAT TCC GAT GCC GGC TCG GAC                 656
Phe Pro Gly Ala Gln Cys Phe Val Tyr Asp Ser Asp Ala Gly Ser Asp
145                 150                 155                 160

AGT GAT GCA CGC AGT AGC ATC GAC GCT GTG ATG CAC GAA GAT ATC GAG                 704
Ser Asp Ala Arg Ser Ser Ile Asp Ala Val Met His Glu Asp Ile Glu
                 165                 170                 175

CTA CCG TCC ACC TTT TGC CGT CCA CAA ACA CCA CAA ACC CAC GAT GTT                 752
Leu Pro Ser Thr Phe Cys Arg Pro Gln Thr Pro Gln Thr His Asp Val
             180                 185                 190

GCC CGT GAC GAG CAT CAT GAT GGG TAT CTT TGC GAT CCC AAA GTT GAC                 800
Ala Arg Asp Glu His His Asp Gly Tyr Leu Cys Asp Pro Lys Val Asp
         195                 200                 205

CAC GCC TCG GTC GCC AGA GAC GTC TTA TCG CTC GGA CGC CAA CGA CAT                 848
His Ala Ser Val Ala Arg Asp Val Leu Ser Leu Gly Arg Gln Arg His
     210                 215                 220

GTA TTC TCA AGC GGC TCC CGA GAG CTC GAC GAC CTG CTA GGC GGT GGG                 896
Val Phe Ser Ser Gly Ser Arg Glu Leu Asp Asp Leu Leu Gly Gly Gly
225                 230                 235                 240

GTG CGT TCC GCT GTG CTC ACC GAG CTC GTC GGT GAA AGC GGC TCT GGT                 944
Val Arg Ser Ala Val Leu Thr Glu Leu Val Gly Glu Ser Gly Ser Gly
                 245                 250                 255

AAG ACC CAG ATG GCT ATC CAA GTT TGC ACT TAT GCC GCT CTC GGC TTG                 992
Lys Thr Gln Met Ala Ile Gln Val Cys Thr Tyr Ala Ala Leu Gly Leu
             260                 265                 270

GTT CCG CTG AGC CAA GCT GAC GAT CAC GAC AAG GGC AAC AAC ACA TTT                 1040
Val Pro Leu Ser Gln Ala Asp Asp His Asp Lys Gly Asn Asn Thr Phe
         275                 280                 285

CAA TCC AGG ACT TTC GTA CGA GAC CCG ATA CAC GCT TCG ACC AAA GAC                 1088
Gln Ser Arg Thr Phe Val Arg Asp Pro Ile His Ala Ser Thr Lys Asp
     290                 295                 300
```

```
GAC ACA CTA AGC GAC ATT CTG CAG AGC TAC GGC ATG GAG CCC TCG ATT    1136
Asp Thr Leu Ser Asp Ile Leu Gln Ser Tyr Gly Met Glu Pro Ser Ile
305                 310                 315                 320

GGA TCT CAC CGC GGT ATG GGC GCG TGC TAC ATC ACA TCT GGT GGC GAG    1184
Gly Ser His Arg Gly Met Gly Ala Cys Tyr Ile Thr Ser Gly Gly Glu
                325                 330                 335

CGC GCA GCG CAT TCG ATC GTG AAC CGA GCT CTG GAA CTT GCA AGC TTT    1232
Arg Ala Ala His Ser Ile Val Asn Arg Ala Leu Glu Leu Ala Ser Phe
            340                 345                 350

GCT ATC AAC GAA CGC TTT GAT CGC GTC TAT CCG GTC TGC GAT CCT ACA    1280
Ala Ile Asn Glu Arg Phe Asp Arg Val Tyr Pro Val Cys Asp Pro Thr
        355                 360                 365

CAA AGC TCG CAG GAC GCC GAT GGG CGC CGC GAC GCA TTG CTG GCC AAG    1328
Gln Ser Ser Gln Asp Ala Asp Gly Arg Arg Asp Ala Leu Leu Ala Lys
    370                 375                 380

GCA CAG CAG CTT GGT CGT CGA CAA GCG CTT GCC AAC TTG CAC ATA GCC    1376
Ala Gln Gln Leu Gly Arg Arg Gln Ala Leu Ala Asn Leu His Ile Ala
385                 390                 395                 400

TGC GTC GCT GAT GTC GAG GCA TTG GAG CAT GCT CTC AAG TAC AGT TTG    1424
Cys Val Ala Asp Val Glu Ala Leu Glu His Ala Leu Lys Tyr Ser Leu
                405                 410                 415

CCT GGC TTG ATT CGT CGA TTG TGG TCG AGT AAG CGT CAG TCG GGC GTA    1472
Pro Gly Leu Ile Arg Arg Leu Trp Ser Ser Lys Arg Gln Ser Gly Val
                420                 425                 430

TCG CGC GAG ATT GGC GTT GTG GTG GTA GAC AAT CTT CCA GCG CTT TTC    1520
Ser Arg Glu Ile Gly Val Val Val Asp Asn Leu Pro Ala Leu Phe
            435                 440                 445

CAG CAA GAT CAA GCG GCA GCG AGC GAT ATC GAC TCG CTC TTC CAA CGC    1568
Gln Gln Asp Gln Ala Ala Ala Ser Asp Ile Asp Ser Leu Phe Gln Arg
        450                 455                 460

TCA AAG ATG CTA GTC GAG ATC GCG GAT GCG CTC AAG CGT ATC AGT GCT    1616
Ser Lys Met Leu Val Glu Ile Ala Asp Ala Leu Lys Arg Ile Ser Ala
465                 470                 475                 480

GTA CAA TGG CGT GGC GCT TCA GAT TGT GGT TCC TCT GCA GGT AGA GCG    1664
Val Gln Trp Arg Gly Ala Ser Asp Cys Gly Ser Ser Ala Gly Arg Ala
                485                 490                 495

GTG CTG GTG CTG AAC CAC GTC AGC GAT GCG TTT GGA ATC GAC AAG CAG    1712
Val Leu Val Leu Asn His Val Ser Asp Ala Phe Gly Ile Asp Lys Gln
                500                 505                 510

ATT GCA CGG CGC TTC GTA TTC GAC TCG GCG CAC CGC ATC CGA ACG CGT    1760
Ile Ala Arg Arg Phe Val Phe Asp Ser Ala His Arg Ile Arg Thr Arg
            515                 520                 525

CGG TCT CAT TTT GCA CGC AAC GAT CCT GGC ACA TCA AGT CAA GCG CCA    1808
Arg Ser His Phe Ala Arg Asn Asp Pro Gly Thr Ser Ser Gln Ala Pro
        530                 535                 540

ACC TCG GCA TTC AGC GGT GGC ACT GGA TCG GCG TTA CCC GAC CAG CCG    1856
Thr Ser Ala Phe Ser Gly Gly Thr Gly Ser Ala Leu Pro Asp Gln Pro
545                 550                 555                 560

CTA GCG ATG GAT GTG GCT AGC CAG ACT GCG TTC ACC AGC GGG CTG CTC    1904
Leu Ala Met Asp Val Ala Ser Gln Thr Ala Phe Thr Ser Gly Leu Leu
                565                 570                 575

GCC TCG ATC GCG CCT ACG CTG GCG GAA GCG GTT GGC GCA CGC GAG CTC    1952
Ala Ser Ile Ala Pro Thr Leu Ala Glu Ala Val Gly Ala Arg Glu Leu
                580                 585                 590

GAC TCG GCG TGC GCT TCC AAC GAT GTG CCG CTC CGC ACA CTT GAA GCA    2000
Asp Ser Ala Cys Ala Ser Asn Asp Val Pro Leu Arg Thr Leu Glu Ala
            595                 600                 605

CGC ACT GCA CAG CTC GGT CAG ACC TGG AGC AAC CTG ATC AAT GTG CGC    2048
Arg Thr Ala Gln Leu Gly Gln Thr Trp Ser Asn Leu Ile Asn Val Arg
        610                 615                 620
```

```
GTG TTT CTG TCC AAA ACG CGC GCC AGG ATA TGC ATG CGC GAC GAT CAG      2096
Val Phe Leu Ser Lys Thr Arg Ala Arg Ile Cys Met Arg Asp Asp Gln
625                 630                 635                 640

GCA CCA GCA TGC GAG CCA GTG CGC CAA AAC ACC AAT CAA CGT GGT ACG      2144
Ala Pro Ala Cys Glu Pro Val Arg Gln Asn Thr Asn Gln Arg Gly Thr
                645                 650                 655

GCG AGC AAG TCG CTC ATG AAT ACG GTG CGC AAA GCG GCG GTG GTC ATC      2192
Ala Ser Lys Ser Leu Met Asn Thr Val Arg Lys Ala Ala Val Val Ile
            660                 665                 670

AAT CCA TTT GGC GCA ACC ATG TTA GAC GTC GGC GTC GAC AAG AGC GCG      2240
Asn Pro Phe Gly Ala Thr Met Leu Asp Val Gly Val Asp Lys Ser Ala
        675                 680                 685

CTG AGA CAG CTA CGG TTT GTC ATT ACG CCG CGC AAA GCG GTG CAT GTG      2288
Leu Arg Gln Leu Arg Phe Val Ile Thr Pro Arg Lys Ala Val His Val
    690                 695                 700

CTG AAT GCG TAT CCA TCG ACA GTG ATG CAT GCC ATG CAT GCG ACC GCT      2336
Leu Asn Ala Tyr Pro Ser Thr Val Met His Ala Met His Ala Thr Ala
705                 710                 715                 720

GAC AGC ACG CCC GCT CCA GAG TCA CAG CAG CAA CAG CGC GCA GCA GAG      2384
Asp Ser Thr Pro Ala Pro Glu Ser Gln Gln Gln Gln Arg Ala Ala Glu
                725                 730                 735

CGC CAC CCA GCG GAG CAA GAG GAC GCC GAT CAA GAC CTC TTC GGA GAA      2432
Arg His Pro Ala Glu Gln Glu Asp Ala Asp Gln Asp Leu Phe Gly Glu
                740                 745                 750

GCG CTG CAA GAG CAT CAC TGG CTA GCC ATC GAC GAG CTC CAA TCG CAC      2480
Ala Leu Gln Glu His His Trp Leu Ala Ile Asp Glu Leu Gln Ser His
            755                 760                 765

ACC ACC GCG CGT CCG ACT TCC CGA GCC GCC CAA GCT GGC T GAGTGAAAGA    2530
Thr Thr Ala Arg Pro Thr Ser Arg Ala Ala Gln Ala Gly
770                 775                 780

TTGACTGAGT CATCTCACGT CTGCGATCCA GAATCCTTCG TATTTCTACA CACATCACAG    2590

GATCGTGTTC GTATTCGCGA TCATATCGTA CACAACTCAA GTTATTGACG TTGAAATGCA    2650

TTCGTGATTC ACGCTTGTAG CATGCTAGAC GCGAGGCAAG TCTCTTTGGC GCTCATGTTT    2710

AAGCTGGCAC AGGCACGAGC GTCGATTCGG GAAAATGGAA AAAAGGAAGA ACGGCACCAA    2770

GATTGACTGT GTTTAAGTTG AGAGCAAATC GACAACAGTG AAGCATGCTA CAAGTTGTCG    2830

AGCTAGGCGC CGATCTGCGC GTCCCATGAT GCTCTCAGCT GCGGTTCGAC GGCGTTCCAG    2890

ATGTGCGACC ATGTGTCGTC GCCCACCTGT GCTCTGAATT GGTCGAGCGC GGATTTGAAC    2950

CAGACCTTGA CTTGTGCGCC GTGGAGGATG TGCTTGGTAG CGTCCGATTT GATCGTTTCG    3010

CTGGCGGCCA ATTTGGTGAA GCCGGTCTGG AAGCCTGCAG CATGGTCTTC GTCGGCGAAC    3070

AGCAGATCCA CGTCTTGCGT CTGCGTCGCC GAGCTGGGCG TGAGCAGCAA CCGCAACAGC    3130

GCTGCGAGCA ATGTTGGCAA CACGCTCACA TTCGGCGCTC GACGCATGGC CGATGAATTC    3190

ACCAACAAGC TCGCAA                                                    3206

(2) INFORMATION FOR SEQ ID NO:2:

(i) SEQUENCE CHARACTERISTICS:
        (A) LENGTH: 781 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Gly Ile Ala Ile Ala Asp Val Gly Cys Ile Ser Lys Arg Ile
 1               5                  10                  15
```

```
Lys Ala Cys Cys Arg Arg Ala Lys Leu Phe Ser Thr Asp Glu Ile Leu
         20                  25                  30

Leu Ser Pro Pro Gln Gln Leu Ala His Val Leu Arg Ile Ser Gln Ala
         35                  40                  45

Asp Ala Asp Leu Leu Leu Gln Val Ala Thr Ser Ala Pro Pro
         50                  55                  60

Pro Ile Ser Val Leu Asp Ala Leu Asn Gly Lys Leu Pro Ala Thr Asn
 65                  70                  75                  80

Leu Asp Gln Asn Phe Phe Asp Ala Val Ala Ala Asp Asp Asp
                 85                  90                  95

Asp Asp Asn Asp Asp Asp Asp Lys Ala Asp Ser Gly Ser Ala Asp
             100                 105                 110

Ala Ser Asp Thr Ser Asp Ala Asp Gln His Leu Asn Asp Ala Arg
         115                 120                 125

Phe Ala Ser Ser Cys Ile Val Pro Pro Thr Gln Gly Tyr Asp Gly Asn
         130                 135                 140

Phe Pro Gly Ala Gln Cys Phe Val Tyr Asp Ser Asp Ala Gly Ser Asp
145                 150                 155                 160

Ser Asp Ala Arg Ser Ser Ile Asp Ala Val Met His Glu Asp Ile Glu
                 165                 170                 175

Leu Pro Ser Thr Phe Cys Arg Pro Gln Thr Pro Gln Thr His Asp Val
             180                 185                 190

Ala Arg Asp Glu His His Asp Gly Tyr Leu Cys Asp Pro Lys Val Asp
         195                 200                 205

His Ala Ser Val Ala Arg Asp Val Leu Ser Leu Gly Arg Gln Arg His
         210                 215                 220

Val Phe Ser Ser Gly Ser Arg Glu Leu Asp Asp Leu Leu Gly Gly Gly
225                 230                 235                 240

Val Arg Ser Ala Val Leu Thr Glu Leu Val Gly Glu Ser Gly Ser Gly
                 245                 250                 255

Lys Thr Gln Met Ala Ile Gln Val Cys Thr Tyr Ala Ala Leu Gly Leu
             260                 265                 270

Val Pro Leu Ser Gln Ala Asp Asp His Asp Lys Gly Asn Asn Thr Phe
         275                 280                 285

Gln Ser Arg Thr Phe Val Arg Asp Pro Ile His Ala Ser Thr Lys Asp
         290                 295                 300

Asp Thr Leu Ser Asp Ile Leu Gln Ser Tyr Gly Met Glu Pro Ser Ile
305                 310                 315                 320

Gly Ser His Arg Gly Met Gly Ala Cys Tyr Ile Thr Ser Gly Gly Glu
                 325                 330                 335

Arg Ala Ala His Ser Ile Val Asn Arg Ala Leu Glu Leu Ala Ser Phe
             340                 345                 350

Ala Ile Asn Glu Arg Phe Asp Arg Val Tyr Pro Val Cys Asp Pro Thr
         355                 360                 365

Gln Ser Ser Gln Asp Ala Asp Gly Arg Arg Asp Ala Leu Leu Ala Lys
         370                 375                 380

Ala Gln Gln Leu Gly Arg Arg Gln Ala Leu Ala Asn Leu His Ile Ala
385                 390                 395                 400

Cys Val Ala Asp Val Glu Ala Leu Glu His Ala Leu Lys Tyr Ser Leu
                 405                 410                 415

Pro Gly Leu Ile Arg Arg Leu Trp Ser Ser Lys Arg Gln Ser Gly Val
             420                 425                 430

Ser Arg Glu Ile Gly Val Val Val Asp Asn Leu Pro Ala Leu Phe
         435                 440                 445
```

```
Gln Gln Asp Gln Ala Ala Ala Ser Asp Ile Asp Ser Leu Phe Gln Arg
    450                 455                 460

Ser Lys Met Leu Val Glu Ile Ala Asp Ala Leu Lys Arg Ile Ser Ala
465                 470                 475                 480

Val Gln Trp Arg Gly Ala Ser Asp Cys Gly Ser Ser Ala Gly Arg Ala
                485                 490                 495

Val Leu Val Leu Asn His Val Ser Asp Ala Phe Gly Ile Asp Lys Gln
                500                 505                 510

Ile Ala Arg Arg Phe Val Phe Asp Ser Ala His Arg Ile Arg Thr Arg
                515                 520                 525

Arg Ser His Phe Ala Arg Asn Asp Pro Gly Thr Ser Ser Gln Ala Pro
                530                 535                 540

Thr Ser Ala Phe Ser Gly Gly Thr Gly Ser Ala Leu Pro Asp Gln Pro
545                 550                 555                 560

Leu Ala Met Asp Val Ala Ser Gln Thr Ala Phe Thr Ser Gly Leu Leu
                565                 570                 575

Ala Ser Ile Ala Pro Thr Leu Ala Glu Ala Val Gly Ala Arg Glu Leu
                580                 585                 590

Asp Ser Ala Cys Ala Ser Asn Asp Val Pro Leu Arg Thr Leu Glu Ala
                595                 600                 605

Arg Thr Ala Gln Leu Gly Gln Thr Trp Ser Asn Leu Ile Asn Val Arg
610                 615                 620

Val Phe Leu Ser Lys Thr Arg Ala Arg Ile Cys Met Arg Asp Asp Gln
625                 630                 635                 640

Ala Pro Ala Cys Glu Pro Val Arg Gln Asn Thr Asn Gln Arg Gly Thr
                645                 650                 655

Ala Ser Lys Ser Leu Met Asn Thr Val Arg Lys Ala Ala Val Val Ile
                660                 665                 670

Asn Pro Phe Gly Ala Thr Met Leu Asp Val Gly Val Asp Lys Ser Ala
                675                 680                 685

Leu Arg Gln Leu Arg Phe Val Ile Thr Pro Arg Lys Ala Val His Val
690                 695                 700

Leu Asn Ala Tyr Pro Ser Thr Val Met His Ala Met His Ala Thr Ala
705                 710                 715                 720

Asp Ser Thr Pro Ala Pro Glu Ser Gln Gln Gln Arg Ala Ala Glu
                725                 730                 735

Arg His Pro Ala Glu Gln Glu Asp Ala Asp Gln Asp Leu Phe Gly Glu
                740                 745                 750

Ala Leu Gln Glu His His Trp Leu Ala Ile Asp Glu Leu Gln Ser His
                755                 760                 765

Thr Thr Ala Arg Pro Thr Ser Arg Ala Ala Gln Ala Gly
770                 775                 780
```

(2) INFORMATION FOR SEQ ID NO:3:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:3:

Met Gly Ser Ser His His His His His His Ser Ser Gly Leu Val Pro
 1               5                  10                  15

Arg Gly Ser His
         20

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:4:

TAGAGGATCC CCGGGTTTTC CCGGGGATCC TCTAGAGTTT TTCTC            45

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: single
        (D) TOPOLOGY: unknown (ii) MOLECULE TYPE: DNA/RNA (ix) FEATURE:
        (A) NAME/KEY: -
        (B) LOCATION: 20..34
        (D) OTHER INFORMATION: /label= a
            /note= ""RNA""

(xi) SEQUENCE DESCRIPTION: SEQ ID NO:5:

TAGAGGATCC CCGGGTTTTC CCGGGGAUCC UCUAGAGTTT TCTC             44

(2) INFORMATION FOR SEQ ID NO:6:

(i) SEQUENCE CHARACTERISTICS:
        (A) LENGTH: 72 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:6:

TTACGAATTC GAGCTCGGTA CCCGGGGATC CTCTAGAGTC GACCTGCAGG CATGCAAGCT  60

TGGCACTGGC CG                                                      72

(2) INFORMATION FOR SEQ ID NO:7:

(i) SEQUENCE CHARACTERISTICS:
        (A) LENGTH: 72 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:7:

CGGCCAGTGC CAAGCTTGCA TGCCTGCAGG TCGACTCTAG AGGATCCCCG GGTACCGAGC  60

TCGAATTCGT AA                                                      72

(2) INFORMATION FOR SEQ ID NO:8:

(i) SEQUENCE CHARACTERISTICS:
    (A) LENGTH: 50 base pairs
    (B) TYPE: nucleic acid
    (C) STRANDEDNESS: single
    (D) TOPOLOGY: unknown (ii) MOLECULE TYPE: DNA (xi) SEQUENCE DESCRIPTION: SEQ ID NO:8:

TTACGAATTC GAGCTCGGTA CCCGGGGATC CTCTAGAGTC GACCTGCAGG          50

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:9:

CCTGCAGGTC GACTCTAGAG GATCCCCGGG TACCGAGCTC GAATTCGTAA          50

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:10:

TTACGAATTC GAGCTCGGTA CCCGGGGATC                                30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:11:

GATCCCCGGG TACCGAGCTC GAATTCGTAA                                30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:12:

GAUCCCCGGG UACCGAGCUC GAAUUCGUAA                                30

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single

```
        (D) TOPOLOGY: unknown (ii) MOLECULE TYPE: DNA (xi) SEQUENCE DESCRIPTION: SEQ ID NO:13:

ACAGCACCAG ATTCAGCAAT TAAGCTCTAA GCC                                    33

(2) INFORMATION FOR SEQ ID NO:14:

(i) SEQUENCE CHARACTERISTICS:
        (A) LENGTH: 44 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:14:

GAATTCGAGC TCGGTACCCG GGGATCCTCT AGAGTCGACC TGCA                        44

(2) INFORMATION FOR SEQ ID NO:15:

(i) SEQUENCE CHARACTERISTICS:
        (A) LENGTH: 4 amino
        (B) TYPE: amino acid
        (C) TOPOLOGY: unknown (ii) MOLECULE TYPE: peptide (ix) FEATURE:
        (A) NAME/KEY: -
        (B) LOCATION: 1
        (D) OTHER INFORMATION: Xaa is Ser or Thr
        (A) NAME/KEY: -
        (B) LOCATION: 4
        (D) OTHER INFORMATION: Xaa is Arg or Lys (xi) SEQUENCE DESCRIPTION: SEQ ID NO:15:

Xaa Pro Xaa Xaa
```

METHODS TO PROMOTE HOMOLOGOUS RECOMBINATION IN EUKARYOTIC CELLS AND ORGANISMS

This application is a continuation of application Ser. No. 08/373,134, filed Jan. 17, 1995, now U.S. Pat. No. 5,780,296.

This invention was made, in part, with government support under RO1 GM 42482 awarded by the National Institutes of Health. The government has certain rights in the invention.

1. FIELD OF THE INVENTION

The present invention concerns the field of recombinant molecular genetics. Particularly, the invention concerns compounds and methods that can be used to promote genetic recombination between an exogenous polynucleotide and a gene in a eukaryotic organism. More particularly, the invention concerns a class of proteins, termed herein Rec2 proteins, and the genes that encode them, REC2 genes. These proteins are ATPases that catalyze the formation of duplex DNA containing strands that were initially present in two separate duplex DNA molecules (dsDNA) or one dsDNA and one single stranded DNA (ssDNA). The formation of these new duplex DNA molecules, termed homologous pairs, is a necessary whenever genetic homologous recombination between DNA molecules occurs.

2. BACKGROUND TO THE INVENTION

2.1. The Need for the Invention and Work of Others

Those skilled in the art of molecular biology recognize that on frequent occasions it is desired not merely to introduce a new polynucleic acid sequence, i.e, a new gene, into a target eukaryotic cell, but further to place this new gene in a defined location and/or to alter or disable a pre-existing gene in the target cell. In other words, not only is a recombinant cell desired but, it is desired that the genetic recombination be between an exogenous polynucleotide and a pre-defined portion of the target cell genome that is homologous with the exogenous polynucleotide.

A solution to this problem has been offered by Capecchi, M. R., 1989, SCIENCE 244: 1288. In the Capecchi technique, homologous recombination is induced by introducing an exogenous polynucleotide into embryonic stem cells. By suitable construction of the exogenous polynucleotide and choice of the target gene, embryonic stem that have undergone homologous recombination can be selectively expanded and thereafter, reaggregated with normal embryonic cells resulting in viable, chimeric embryos that can develop into fertile adults. The germ line of these founder generation animals contain the recombinant embryonic stem cells. Thus, their offspring includes recombinant animals. By this method, it is possible to construct transgenic animals having particular, pre-defined genetic recombination. Chisaka, O., and Capecchi, M. R. 1991, NATURE 350: 473. The same result can be obtained, with considerably more effort, by direct injection of homologous polynucleotides into the pronucleus of an ova. Brinster, R. L. et al., 1989, PROC.NATL.ACAD.SCI 86: 7087. See also U.S. Pat. No. 4,873,191 to T. E. Wagner and P. C. Hoppe. Implementation of both the Capecchi technique and ovum pronuclear injection can be burdensome owing to the low rate of homologous recombination compared to the rate of "illegitimate" recombination, i.e., recombination between non-homologous DNA molecules. For example, in embryonal stem cells illegitimate recombination following introduction of an exogenous polynucleotide appears to be about 1,000 times more prevalent than homologous recombination. Thomas, K. R., and Capecchi, M. R., 1987, CELL 52: 503–12, while Brinster screened approximately 500 transgenic mice to find a single homologous recombinant. To cope these difficulties it may be necessary to isolate many recombinant clones, prepare and analyze by restriction mapping or sequencing genomic DNA from each in order to identify the homologous recombinant of interest or to design complex selection schemes that differentiate between illegitimate and homologous recombinants. For these reasons those skilled in the art appreciate that there is a need for a method to promote homologous recombination in eukaryotic cells.

Attempts have been made to use RecA, a protein that promotes homologous recombination in prokaryotic cells, e.g., E. coli, to promote homologous recombination in eukaryotic cells. However, these attempts have not been clearly successful. For example U.S. Pat. No. 4,950,599 to W. Bertling discloses no enhancement in the rate of homologous recombination by use of RecA in eukaryotic cells. Patent publications WO 93/22443 to D. Zarling and E. Sena, and publication 94/04032 to D. C. Gruenert and K. Kunzelmann both purport to correct a genetic defect in a cultured cell line related to cystic fibrosis. These publications disclose primarily experimental data that purport to demonstrate a principle rather than data concerning examples of operative methods. Thus, to allow the exogenous polynucleotide/RecA complexes access to the nucleus, Zarling and Gruenert employ cells that were membrane-permeabilized, although such cells are incapable of further growth. Moreover, even when RecA-promoted homologous recombination was asserted to have taken place in intact cells, these publications provide no quantitative estimates of its frequency. Thus, the use of prokaryotic recA has not been convincingly shown to result in a rate homologous recombination in any viable eukaryotic cell significantly greater than the spontaneous rate of homologous recombination.

2.2. The Recombinase from *Ustilago maydis*

*Ustilago maydis* (hereinafter Ustilago) is a fungus, from which the recombination and DNA repair deficient mutants, rec1 and rec2, have been isolated. Holliday, R., 1967, MUTATION RESEARCH 4: 275–288. The rec1 mutant is defective in DNA repair, recombination, growth, and meiosis. Holliday R., et al., 1976, GENET.RES. 27: 413–53. The rec2 mutation displays a normal rate of spontaneous mitotic recombination but very low rates of homologous recombination. A diploid homozygous defective rec2 organism cannot complete meiosis (reduction division). Holliday, R., 1967, MUTATION RES. 4: 275–88; Fotheringham, S., and Holloman, W. K., 1991, GENETICS 129: 1053–60.

An enzymatic activity was isolated from the cytoplasm of Ustilago that promoted the pairing, in the presence of ATP, of single stranded DNA and the homologous linear or supercoiled dsDNA. The same isolate contained an activity that promoted pairing between circular ssDNA and homologous supercoiled DNA and linear dsDNA containing long containing homologous sequences flanked by long stretches of heterology. Kmiec, E. B., and Holloman, W. K., 1983, CELL 33: 857–64; 1984, CELL 36: 593–98. Pairing activity was also observed between two duplex circles under conditions where there was either active transcription, a previously formed homologous pairing between dsDNA and ssDNA, i.e., a "D-loop", or the presence of sequences that allowed the formation of the Z-DNA conformation. Kmiec, E. B., and Holloman, W. K., 1986, CELL 44: 545–54. The pairing (or recombinase) activity was attributed to a single protein with an apparent molecule weight of 70 Kd on SDS-PAGE, which protein comprised about 85–90% of the protein in the most homogeneous fraction. Kmiec, E. B., and Holloman, W. K., 1994, EUR.J.BIOCH. 219: 865–875.

The isolated activity could not be. obtained from fractions of rec1 mutant Ustilago. Similarities were noted between the phenotypes of the rec1 mutant and the recA mutant of *E. coli*, and similarities between the above-described activity from Ustilago and the activity of the RecA protein. For these reasons the homologous pairing activity was attributed to a "rec1" protein. However, as will be explained more fully below this attribution is incorrect.

The normal counterpart of the gene effected in the rec1 and rec2 mutations have been isolated from Ustilago genomic libraries. A genome library from wild type Ustilago was constructed in a vector that autonomously replicates in ustilago. A stock of mutants is transfected with the library and clones that complement the mutant were isolated. The correspondence between the inserts of the isolated clones and the REC1 and REC2 genes were confirmed by showing that each mutant expresses an abnormally sized MRNA, homologous with the identified insert. The REC1 gene was determined by this method to encode an mRNA of about 1.7 kb. Tsukuda, R., et al., 1989, GENE 85: 335–41. The REC2 gene was determined to encode an mRNA of about 2.8 kb. The protein it encodes possesses some regions of homology with the bacterial RecA and yeast proteins Dmc1, Rad51 and RAd57. Bauchwitz, R., and Holloman, W. K., 1990, GENE 96: 285–288; Rubin, B. P. et al., September 1994, MOL.CELL.BIOL. 14:6287–96.

2.3. Maturation Promoting Factor ($P34^{cdc2}$) and its Substrates

The regulation of the growth of eukaryotic cells and particularly the coordination between the replication of a cell's genome (S phase) and the orderly division of that genome into two or four daughter cells (mitosis and meiosis) is accomplished by multiple protein phosphorylations and dephosphorylations catalyzed, respectively, by kineses and phosphatases. The major kinase activity is due to a class of heterodimeric proteins with a common chain, $p34^{cdc2}$, having the enzymatic activity. The second chain of the kinase is a regulatory chain that has been identified as either a cyclin-A or -B-type protein. The substrate specificity of $p34^{cdc2}$ kinase activity is controlled by the associated cyclin. As their name implies, cyclins are unstable proteins the level of which vary throughout the cell cycle. Varying levels of cyclins appear to regulate the beginning not only of mitosis or meiosis but also the onset of S phase. In yeast, there are at least 8 cyclin proteins.

Substrates of $p34^{cdc2}$ include H1 histone, nuclear envelope proteins (lamins), the proto-oncogen $pp60^{src}$, and the transforming protein of the tumor virus SV40. Reviewed Lewin, B., 1990, CELL 61: 743–52; Reed, S. I., 1992, ANN.REV.CELL BIOL. 8: 529–61; Pines, J., 1994 NATURE 371: 742. The different substrate proteins $p34^{cdc2}$ kinase are phosphorylated at different phases of the cell cycle. When the target of $p34^{cdc2}$ phosphorylation has an identified enzymatic function, e.g., $pp60^{src}$, phosphorylation is associated with activation of the target protein's enzyme activity, though the phosphorylation does not necessarily directly cause activation of enzyme function. Shenoy, S., et al., 1992, PROC.NATL.ACAD.SCI. 89: 7237–41.

The consensus phosphorylation site of $p34^{cdc2}$ kinase action is the sequence (Ser or Thr)-Pro-any amino acid-(Arg or Lys)-, the Ser/Thr being phosphorylated. Shenoy, S., et al., 1989, CELL 57: 763–74. While it is clear that the replacement of the Ser/Thr in the consensus site by any other amino acid would block the action of $p34^{cdc2}$ kinase, and hence, block its regulation of the activity of the mutant protein (mutein), it is, in general, unpredictable whether such a mutein would be supra-active or inactive.

3. SUMMARY OF THE INVENTION

The present invention comprises: a genus of proteins, collectively termed Rec2, a species of which is found in every eukaryote; super-active muteins of those proteins; vectors suitable for the expression of both the naturally occurring and mutant proteins in prokaryotes and eukaryotes and methods of recovering the protein in active form; and methods of using isolated Rec2 protein and REC2-containing expression vectors to promote homologous recombination in eukaryotic cells. The application discloses the novel REC2 genes of mouse, human and yeast.

The invention is useful to promote homologous recombination in cultured cells for such purpose of: making specific genetic alterations in cells used to produce a recombinant protein; introducing specific alterations in embryonic stem cells or ova (gametes) to be used in the construction of transgenic animals; modifying in vitro explanted tissue stem cells, e.g., hematopoietic stem cells, which can then be continued in culture, or reimplanted into a non-human host, to produce a specific product, or reimplanted into a human subject in need of gene therapy for a medical condition amendable thereto. The methods and compounds of the invention can also be employed to promote homologous recombination within an animal including a human.

BRIEF DESCRIPTION OF THE FIGURES

FIGS. 1A–1D. The nucleic acid sequence of Ustilago REC2 with annotated derived amino acid sequence (Dayhoff code).

FIG. 2. The composite amino acid sequence of Ustilago REC2 derived from direct Edman degradation of the isolated protein and by inference from the nucleic acid sequence.

FIG. 3A: 20 μM denatured P22 [$^3$H]DNA (as nucleotide) either in the presence of 1 mM ATP (circles) or with no ATP (triangles); FIG. 3B: in the presence (dots) or absence (triangles) of 20 μM M13 DNA.

FIG. 4A: Identical strand pairing to a 33-mer identical with M13. In the absence of M13 single-stranded DNA the background of $^{32}$P label retained was usually 5% of the input labeled oligonucleotide. Results are corrected for this background. (closed circles) complete reaction; (closed triangles) φX174 DNA in place of M13 DNA; (closed squares) complete reaction plus 5 mM ADP; (open triangles) complete reaction minus ATP; (open circles) complete reaction treated with 100 μg/ml proteinase K for 10 min. FIG. 4B: Complementary strand pairing to a 44-mer. (closed circles), complete reaction; (closed triangles), complete reaction treated with proteinase K for 10 min.

FIG. 5A DNA/DNA hybrids; (circles) 72-mer; (triangles) 50-mer;

(squares) 30-mer. FIG. 5B: RNA/DNA hybrids using 30-mer duplexes. DNA/RNA hybrid (circles); DNA/DNA hybrid (squares); (triangles) RNA/DNA hybrid in reaction with M13mp18 single-stranded RNA.

5. DETAILED DESCRIPTION OF THE INVENTION

Figure 3A:
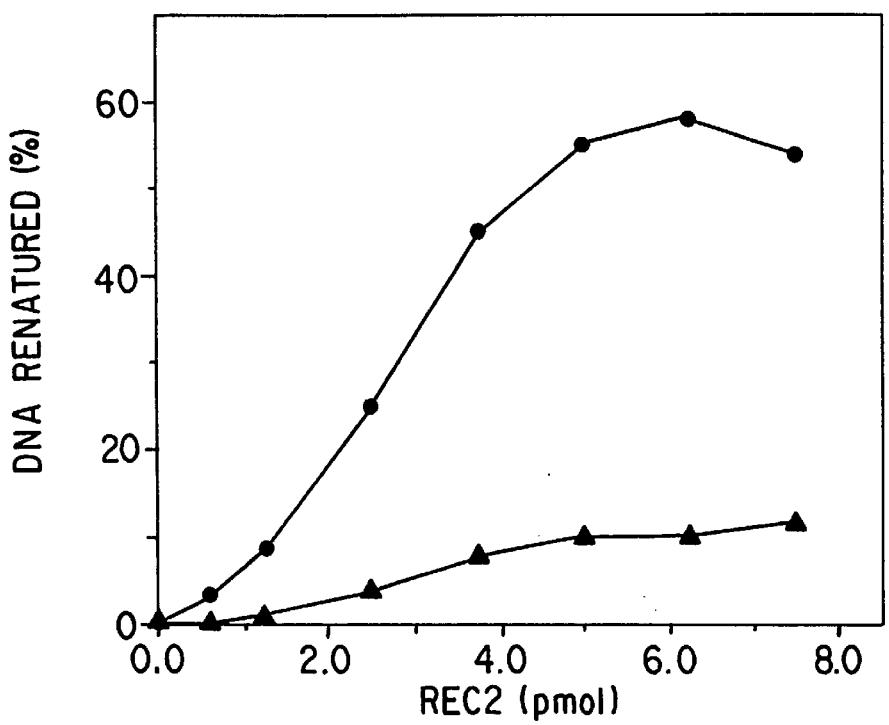
FIGS. 3A and 3B. DNA renaturation and ATPase activities of recombinant REC2 protein.

The present invention is based, in part, upon the unexpected result that the gene that encodes the Ustilago homologous pairing (recombinase) activity is encoded by the REC2 gene. The protein associated with the isolated recombinase activity described hereinabove, was a truncated form of Ustilago Rec2. Based on the identification of REC2 as encoding a homologous pairing (recombinase) enzyme, genes encoding the recombinases of yeast, mice and humans have been identified.

The present application teaches that Rec2 contains a single $p34^{cdc2}$ kinase phosphorylation site that includes $Thr^{697}$. The invention is further based, in part, on the unexpected discovery that the mutein of Rec2, in which the wild-type $Thr^{697}$ residue is replaced by an aliphatic residue ($T \rightarrow A^{697}$), hereinafter $Rec2^{super}$, causes supra-normal rates of homologous recombination when expressed in wild-type Ustilago. The invention encompasses Rec2 and $Rec2^{super}$ proteins and $REC2^{super}$ genes from Ustilago. The application discloses methods of cloning homologs of REC2 from other species and specifically encompasses the REC2 homologs of *Saccharomyces cerevisiae*.

The invention also encompasses methods of using expression vectors to introduce, into a target cell of interest, wild-type and $T \rightarrow A^{697}$ REC2 genes as well as methods of using purified Rec2 and $Rec2^{super}$ proteins to augment the rate of homologous recombination. The invention further encompasses the use of mixed polydeoxyribo/ribonucleic acids, as exogenous polynucleotide substrates for Rec2 recombinases.

The purpose of the present invention is to provide a method whereby preselected genes in a target cell can be altered. A gene in a target cell is altered by homologous recombination with an exogenous polynucleotide, that contains a region that differs from the target gene. Hereinafter, when references are made to an exogenous polynucleotide, exogenous nucleic acid or exogenous ssDNA, that is homologous with a target gene, it is to be understood, without explicit recitation, that a portion of the sequence of the exogenous polynucleotide, etc., is homologous with a portion of the target gene and that interposed between the portions homologous to the gene is a heterologous portion so that homologous recombination between the polynucleotide and the target gene effects an alteration its sequence.

The types of cells in which genetic modifications can be made using the invention include all eukaryotic cells. In one embodiment, the cells are yeast or fungal cells such as *Saccharomyces cerevisiae* or *Ustilago maydis*. In alternative embodiments, cells of higher eukaryotes can be used, such as: human tissue-specific stem cells and precursor cells, including hematopoietic stem and precursor cells; ova cells that are suitable for the preparation of transgenic animals such as transgenic mice, rats, swine and cattle; and embryonal stem cell lines such as CC1.2. See Bradley, A., et al., 1984, NATURE 309: 255–56. In addition to the ex vivo embodiments, the invention can be advantageously employed in vivo to promote homologous recombination in any cell type into which exogenous DNA can be introduced and expressed. The invention can be employed to promote homologous recombination in cell types that are not proliferating, such as, for example, liver cells and neuronal cells of the central and peripheral nervous system. The invention can also be used to promote homologous recombination in cell types that are actively proliferating such as the mucosal cells of the gut and respiratory system.

The present invention can, in a further embodiment, be employed to target specific genes that arise by the translocation of genetic elements, such as occurs normally in lymphoid cells and, pathologically, in many types of neoplasms. Because such translocations create DNA sequences, not found in other cells, homologous recombination occurs only within the specific cell lineage containing the translocation. According to the inventor, the exogenous nucleic acid can be constructed to introduce a sequence that would lead to the disruption of the expression of the unique sequence, such as, by way of example, a splice donor or splice acceptor site or, if the unique sequence is located close to an exon of the gene, the exogenous nucleic acid can be used to introduce a frame shift mutation or stop codon, disrupting expression of the translocated gene.

5.1. REC2 Genes and Methods of Cloning Homologs of Ustilago REC2

Genes that are homologous with Ustilago REC2 can be cloned from any eukaryotic species by screening genomic libraries or cDNA libraries of mitotically and/or meiotically active tissue, e.g., from testicular libraries or from other rapidly dividing cells, from the species by a variety of techniques. The libraries can be screened by hybridization with a probe that consists of the entire REC2 gene or fragments thereof.

Genome blots of Saccharomyces, a genus of the type Ascomycepes yeast form fungi, which type excludes Ustilago strongly and specifically hybridizing bands. This result indicates that the REC2 genes of any species of the Ascomycepes group can be cloned directly from a genome library or by band cloning of a genomic digest.

Although genomic of mammalian species do not demonstrate any strongly hybridizing bands, blots of poly $A^+RNA$ from murine and human sources do display a 3 kb transcript that hybridizes to a Ustilago REC2 probe. This result is confirmed by the recovery of hybridizing clones from a λgt10 cDNA library made from a human lymphoma cell line. Mammalian REC2 genes can be isolated and identified by hybridization, isolation and sequencing of the isolated cDNA clones from species such as, without limitation, human, mouse, guinea pig and hamster.

Alternative methods to isolate putative REC2 genes from other species of eukaryotes utilize the paired sense and antisense oligonucleotides, the sequences of which encode, or are complementary to nucleic acids encoding, the portions of Rec2 that are highly conserved among species. One such portion consists of residues 226–270, which shows homology with *S. cerevisiae* proteins Dmc1, Rad57 and Rad51 and with the *E. coli* protein RecA. The oligonucleotides are selected to bracket portions of the gene of about 100 to 500 bp. The paired oligonucleotides can be used as primers in a polymerase chain reaction (PCR) to amplify the bracketed fragment of the gene. The amplification products may then be cloned, sequenced and those, the sequence of which indicates that they are fragments of a Rec2 gene, can be used as probes to isolate the entire gene from a suitable library.

The identity of a clone that hybridizes with a Ustilago REC2 probe (hereinafter a "putative REC2 gene") can be determined by expressing the gene in a prokaryotic expression system, isolating and assaying the product according to the methods set forth hereinafter. The finding of any of the activities of promoting complementary or identical strand pairings, or homologous recombination confirms that the putative gene is a REC2 gene. Alternatively, the putative gene can be sequenced and the sequence compared by use of any of the sequence comparison algorithms known in the field. The FASTA algorithm of Pearson is suitable. Pearson, W., 1990, METHODS IN ENZYMOLOGY, 183: 63 (Academic Press, San Diego, Calif.; Pearson, W. et alia, 1988, PROC.NATL.ACAD.SCI. 85: 2444.

Procedures for the comparison of the sequences of putative Rec2 proteins from species other than Ustilago with the sequence of Ustilago Rec2 are well known to those skilled in the field. The procedure to calculate a "normalized alignment score" is described by R. F. Doolittle, 1981, Science 241: 149 (see particularly pages 154–155), which is hereby incorporated by reference in its entirety. A putative REC2 gene having a normalized alignment score, when compared with Ustilago Rec2, of greater than 150 and having an A motif and a B motif as indicated in FIGS. 1A–1D, can be tested to determine whether it is a recombinase. Useful tests of a potential recombinase include genetic complementation tests to determine whether the putative gene complements the defects in the REC2-1 gene of Ustilago and biochemical tests of the protein product of the putative REC2 gene that test whether the protein is an ATPase and catalyzes the formation of complementary or identical strand pairings of polydeoxynucleic acids.

A putative REC2 gene having a normalized alignment score of about 200 or greater when compared with the entire sequence of Ustilago Rec2 can be considered a homolog of REC2 gene.

5.2. The Production and Isolation of REC2 from a Recombinant Expression System According to the present invention a Rec2 protein can be produced from any full length REC2 gene or cDNA. In the first step of the process to produce Rec2 protein, the sequence surrounding the initiation codon of REC2 is modified by insertion of a restriction site, e.g., a NdeI site (5'-CA/TATG-3'). Such a modification can be accomplished by PCR using a near homologous primer. Using this restriction site the amplified REC2 gene can be inserted into an expression vector immediately 3' to a hexahistidine encoding sequence. The pET expression system vector (Novagen, Inc., Madison, Wis.) or equivalent are suitable. Expression systems wherein the REC2 gene is operably linked to the polyhedrin promoter of the baculovirus *Autographica californica* virus which is then grown in insect cells from the fall armyworm, *Spodoptera frugiperda*, are also suitable for the expression of the Rec2 protein.

When expressed in *E. coli* the Rec2 protein can be recovered as an active recombinase by the following procedure. After induction of Rec2 protein production, the bacterial cells are harvested, sonicated and the soluble supernatant (15,000 rpm×20 min, Sorvall SS34) discarded. The pellet is then solubilized in a high NaCl (about 0.2–1.0 M), mildly alkaline (ph 7.9) buffer containing a chaotropic denaturing agent, e.g., 8 M urea, 6 M guanidine HCl or the like. The material that remains insoluble after exposure to the chaotropic buffer is discarded and the solubilized material is passed over a nitrilotriacetic acid agarose column that had been loaded with $Ni^{++}$ (NTA-agarose) (Qiagen, Chatsworth, Calif.) or its equivalent. When expressed in a baculovirus system the protein can be solubilized by any method and passed over that NTA-agarose column so that the recombinant Rec2 protein is bound.

The material specifically bound to the NTA-agarose is eluted by high imidazole, recovered and dialyzed into a moderately alkaline Tris buffer (pH 8.5) saline (0.05–0.2 M NaCl) buffer (TNE buffer) containing 6 M urea or similar chaotropic agent for at least 1 hour and preferably at least 3 hours. The chaotropic agent is then slowly diluted by dialysis against an increasing volume of TNE without chaotropic agent. The initial dialysis is performed with a dialyzing volume equal to the dialysate (sample) volume; the dialyzing volume is slowly increased, at a uniform linear rate, until a final volume of 20× the initial dialysate is reached over a period of at least 5 hours. Recombinant Ustilago Rec2, so prepared has an apparent molecular weight of 110 Kd, when electrophoresed on SDS-PAGE, and an actual molecular weight of 84 KD.

The recombinant Rec2 protein of any eukaryotic species, so prepared, is suitable for use in the invention. In the presence of ATP, a Rec2 protein will cause the pairing and transfer of the ssDNA accompanied by the hydrolysis of the ATP. Thus, the activity of the recombinant protein may be assessed by assaying the formation of complexes between homologous linear dsDNA and circular ssDNA or by assaying its ATPase activity. Either dsDNA or ssDNA acts as a cofactor for the ATPase activity. Quantitatively, the ATPase activity of the Rec2 of the present invention is greater than 4 moles ATP/min per mole of protein and usually between about 5–400 mole ATP/min per mole of protein when 50 µM M13mp18 ssDNA are present and the other assay conditions are 25 mM Tris pH 7.5, 10 mM $MgCl_2$, 1 mM DTT and 0.5 mM [α-$P^{32}$]ATP. Kmiec, E. B., and Holloman, W. K., 1994, EUR.J.BIOCH. 219: 865–875. Those skilled in the art appreciate that protein prepared according to the present invention can contain a substantial fraction of denatured and, hence, enzymatically inactive protein. The above-described specific activities refer to the activity of the aggregate product not to the specific activity of the active component within the product.

5.3. The Removal of the $P34^{cdc2}$ Phosphorylation Site to Augment Recombinase Activity The REC2 genes of the invention contain $P34^{CDC2}$ kinase consensus phosphorylation site, which is a tetrapeptide (Ser/Thr)-Pro-Xxx-(Arg/Lys)-, wherein the residues in parentheses are alternatives at a position and "Xxx" indicates any amino acid may be present. Ustilago Rec2 contains a $P34^{CDC2}$ kinase consensus phosphorylation site which begins at $Thr^{697}$, the phosphorylated amino acid. To prevent the potential regulation by $P34^{CDC2}$ of the action of Rec2, $Thr^{697}$ can replaced by any amino acid except Ser; replacement by an amino acid such as glycine or alanine is preferred. Site directed mutagenesis may be conducted by any method. The method of Ho, S. N., et al., GENE 77: 51–59 (herewith incorporated by reference in its entirety), is suitable. According to the method of Ho, overlapping, mutated genome fragments are synthesized in two separate PCR reactions. Of the four primers are used in the two reactions, two are complementary to each other and introduce the desired mutation. The PCR reactions are performed so that the 3' end of the sense strand of one product is complementary to the 3' end of antisense strand of the other. The two PCR products are denatured, mixed and reannealed. The overlapping partial duplex molecules are then extended form a full length dsDNA, amplified in a third PCR reaction, the product isolated and inserted by conventional recombinant techniques into the parent gene.

Unexpectedly, the replacement of $Thr^{697}$ by Ala results in a Rec2 (hereinafter $Rec2^{super}$) that is 8–10 fold more active in Ustilago than the wild type Rec2. Further, while the introduction of multiple copies of REC2 into Ustilago does not result in increased homologous recombination, except in $REC2^-$ deficient organisms, the introduction of a $REC2^{super}$ expression vector results in an 8–10 fold increase rate of homologous recombinants even in wild-type Ustilago. The advantages of using a $REC2^{super}$ expression vector depend upon the physiological state of the $P34^{CDC2}$ site in the cell-type of interest. The practitioner's choice between the use of Rec 2 and $Rec2^{super}$ proteins or expression vectors, thus, depends upon the cell-type to be transfected and the practitioner should investigate which is appropriate for her intended use.

5.4. The Use of REC2-Containing Eukaryotic Expression Vectors to Promote Homologus Recombination of Genetic Material Linked and Unlinked to the Expression Vector In one embodiment of the invention homologous recombination between a targeted gene of a cell and an exogenous nucleic acid homologous with the targeted gene is effected by simultaneously introducing a vector that expresses Rec2 or $Rec2^{super}$ and the exogenous nucleic acid. The exogenous nucleic acid and the REC2 gene can be present on the same molecule (linked) or can be present as separate molecules. The optimum concentration of REC2 expression vector and, when the expression vector and the exogenous nucleotide are unlinked, the ratio between vector and exogenous nucleic acid can be determined by targeting a selectable target gene in the cell of interest and determining the optimal amount and ratio for that gene. The optimal amount of expression vector and the ratio of expression vector to exogenous nucleic acid is a function of the cell type and the size of the exogenous nucleic acid.

5.4.1. The Construction of Expression Vectors Having Promoters Active in Mammalian Cells The REC2 gene of the invention can be expressed in a mammalian cell by any expression system that places a REC2 gene in operable linkage with a promoter which is active in the mammalian cell. As used herein a promoter includes both the initial binding site of the RNA polymerase, which is alternatively termed a TATA box or a Goldberg-Hogness box, and the upstream promoter elements, which frequently contain the sequences CAAT or CACC. Promoters suitable for the expression of REC2 in mammalian cells include promoters obtained from mammalian viruses such as Cytomegalovirus, SV40 and Moloney Leukemia Virus. Further augmentation of the transcription level of REC2 genes can be obtained by use of enhancer sequences.

5.4.2. Methods of Introducing the Vector and the Targeted Nucleic Acid Into the Cell Any method that is suitable for introducing nucleic acid into a cell may be used. Such methods include by way of example electroporation, liposomal delivery, calcium phosphate precipitation. Replication defective viral particles, such as: adeno-associated virus, see, e.g., U.S. Pat. No. 5,354,678 to Lebkowski and U.S. Pat. No. 5,139,941 to Muzcyzka; adenovirus, see, e.g., WO 94/08026 to Kahn, A. and others, and WO 94/10322 to Herz, J.; or herpes amplicon vectors see, e.g., WO 90/09441 and WO 92/07945 to Geller, A. I., can also be used to introduce a REC2 gene and a linked exogenous nucleic acid. Scientific publications concerning adenovirus and adeno-associated virus can be found at Crystal, R. G. , et al., 1994, NATURE GENETICS 8: 42; and Kaplitt, M. G. et al., 1994, NATURE GENETICS 8: 148, respectively.

5.5. The Use of Isolated Rec2 Protein to Promote Homologous Recombination

In an embodiment of the present invention, Rec2 can be used to promote recombination between a target gene and an exogenous ssDNA molecule that is homologous with a portion of the gene. The length of the DNA molecule can be between about 25 nt and 1 kb. In a preferred embodiment the there are between about 10 nt and about 40 nt of homologous sequence flanking a non-homologous portion of the exogenous ssDNA. The non-homologous portion can be between 1 nt and 1 kb. In a preferred embodiment the ssDNA is about 50 nt in length and the non-homologous portion is 1 nt in length. A mixture of Rec2 protein to exogenous ssDNA having a molar ratio of between 1:1 and 50:1 can be used for the practice of the invention, a mixture of 5:1 to about 10:1 is preferred for the practice of the invention when the exogenous ssDNA is about 50 nt in length. Proportionately more Rec2 can be used when the exogenous ssDNA is longer.

Recombinant Rec2 is prepared according to the invention. A complex of ssDNA and Rec2 is preformed in a small volume. For example, a mixture at ssDNA (50 nt) at about 20 ng/$\mu$l and a 10× excess of Rec2 will form complexes suitable for the practice of the invention when incubated about 10 minutes at 31° C. in a solvent of 2 mM Tris (pH 7.5). Proportionately longer incubations can be employed if the concentration of Rec2 is reduced.

The complex can be introduced by any means effective to introduce protein/DNA complexes into the cell type of interest, so long as the method does not cause the denaturation of the Rec2. In one embodiment the Rec2/ssDNA complex can be introduced by electroporation. To facilitate electroporation the Rec2 protein can be dialyzed into low ionic strength buffer prior (e.g., 2 mM Tris pH 7.50 or distilled water) prior to the formation of the Rec2/ssDNA complexes.

5.6. The Use of RNA/DNA Chimeric Oligonucleotides to Promote Homologous Recombination In an alternative embodiment of the invention the exogenous polynucleotide can be a mixed nucleic acid containing ribonucleotides and deoxyribonucleotides, the two strands of which are covalently linked by a single stranded tetranucleotide, hereinafter a "hair-pin" linkage. Small self-complementary, hair-pin linked, polydeoxynucleotides, having a duplex sequence length of about 15–20 bp do not participate in homologous recombination. Their inactivity is not due to the presence of the hairpin sequence linking the strands. However, if, in one strand of the duplex, the deoxynucleotides are replaced by ribonucleotides to produce a self-complementary "chimeric-polynucleotide" the resultant molecule (hereinafter "mono-chimeric exogenous polynucleotide") can be a substrate irecombiomologous recombination process. This invention is disclosed in commonly assigned, copending U.S. patent application Ser. No. 08/164,303, which is incorporated herein by reference in its entirety. Further embodiments of the invention are disclosed in U.S. patent application Ser. No. 08/353,651, filed Dec. 9, 1994, by Eric B. Kmiec, entitled: "COMPOUNDS AND METHODS FOR SITE DIRECTED MUTATIONS IN EUKARYOTIC CELLS," which is hereby incorporated by reference in its entirety. In these latter embodiments a non-homologous nucleic acid is interposed between two chimeric polynucleotides, the ends of which are hair-pin linked together so as to form a single closed-end substantially self-complementary linear duplex nucleic acid having two distinct regions of RNA/DNA chimerism. Such molecules are hereinafter termed "di-chimeric exogenous nucleic acids". The size of the non-homologous DNA insert can be up to about 1 kb. The resultant molecule consisting of two chimeric-polynucleotide regions of about 20–50 bp in length separated by a DNA insert of up to about 1 kb.

In an embodiment of the present invention an expression vector suitable for Rec2 production is introduced into the target cell accompanied by the either mono-chimeric or di-chimeric nucleic acids. The ratio of expression vector to exogenous chimeric nucleic acid to be used is between 1:1 and $1:10^4$. In an alternative embodiment complexes between a Rec2 protein and the chimeric exogenous nucleic acids are preformed, according to the teaching of Sect. 5.5 supra.

6. EXAMPLES

6.1. The Identification of Ustilago Recombinase Activity and the REC2 Gene Product The REC2 gene was cloned by complementation of the rec2–1 mutant. A Ustilago genome library was made using a vector that autonomously replicates in Ustilago. Bauchwitz, R., and Holloman, W. K., 1990, GENE 91: 285. This DNA sequence and the deduced protein sequence is given in FIGS. 1A–1D. See also Rubin, B. P., et al., September 1994, MOL.CELL.BIOL. 14: 6287–96.

The identification of the Rec2 gene product and the recombinase activity isolated from Ustilago was made as follows. The major protein species in the most homogeneous Ustilago fractions having recombinase activity was subjected to Edman degradation sequencing. In addition, this protein was subjected to tryptic proteolysis and 5 major peptides isolated. Edman degradation sequencing of these peptides was then performed. In FIG. 2 the same protein sequence as FIGS. 1A–1D is presented and, additionally, in bold large capital letters, are shown the sequences which were obtained by Edman degradation of the protein from the recombinase active fractions. There are 5 sequences from the tryptic peptides, between 6 and 9 residues in length, and the two "N-terminal" sequences, 9 and 10 residues respectively. These sequences clearly established that the REC2 gene encodes the major protein in the Ustilago recombinase isolate. The "N-terminal" sequence data further indicate that the protein present in the Ustilago recombinase isolate was not native Rec2, but was a mixture of two different truncated proteins lacking the N-terminal 129 residues or 153 residues, respectively.

Cells having a rec2 mutation were transfected, a wild-type revertant isolated and the episome insert encoding the presumptive Rec2 protein cloned and sequenced.

The activity of the Ustilago recombinase isolate had been detected only in vitro experiments using isolated components, not in assays involving living cells. The protein in the active isolate lacked both the nuclear localization sequence (NLS), residues 14–17, and the Chromatin Binding Motif (CBM), residues 93–103, regions which are predicted to be necessary for normal function of a eukaryotic recombinase. This prediction is supported by the observation that although extracts from the rec2–1⁻mutant, which has a deletion of the N-terminal region of REC2 spanning both the NLS and CBM regions, could be used to obtain active recombinase isolates, there cells that did not, of course, have normal levels of Rec2 activity in vivo. Thus, it appears very likely, if not certain, that the protein fractions, isolated according to the method of Kmiec, E. B., and Holloman, W. K., 1983, CELL 33: 857–64, and Eur.J.Bioch. 219: 865, were unable to promote homologous recombination in eukaryotic cells.

6.2. Genomic Blots for REC2

In preliminary studies genomic DNA from Ustilago, Saccharomyces, *Aspergillus niger*, mouse and human was digested with EcoR1, BamH1 and Hind III and electrophoresed in 0.8% agarose, transferred to a ZETAPROBE membrane. The membrane was probed with radiolabelled 2.8 kb REC2 insert obtained from the plasmid pCM349 (pET14b-REC2). The membrane was washed in low stringency conditions (40 mM $Na_2PO_4$ 1 mM EDTA, 1% SDS at 50° C.). Strong hybridization was observed in the Ustilago, Saccharomyces, Aspergillus lanes, but not in the mouse or human. Saccharomyces fragments of the following sizes were observed: EcoR1, 5 bands 3.8, 2.9, 2.4, 2.0, and 1.6 Kb; Hind III, 3 bands of 3.8, 2.9, 1.6 Kb; and BamH1 bands of 3.4 Kb and 1.8 Kb.

6.3. The Production of Recombinant REC2 From Ustilago

The 2.5 kb NdeI-XhoI fragment containing Ustilago REC2 was engineered with the NdeI site at the initiation codon using the 2.8 kb BamH1 Ustilago genomic fragment. The NdeI-XhoI fragment was inserted into the corresponding cloning sites in pET-14b (Novagen, Madison, Wis.) to yield pCM349. Bacteria carrying pCM349 were deposited in the ATCC as accession No. 69737 on Jan. 5, 1995. The plasmid pCM349 encodes a Rec2 protein having a leader peptide "MGSSH₆SSGLVPRGSH/M etc. (SEQ ID NO:3) which contains a hexahistidine sequence and a thrombin cleavage site (underlined).

*E. coli* transformed with pCM349 were grown in 2xYT (8 g tryptone, 5 g yeast extract, 5 gNaCl per liter) medium containing 35 μg/ml chloramphenicol and 100 μg/ml ampicillin at 37° C. At $A_{590}$=0.6 isopropyl-thio-β-D-galactopyranoside (Sigma Chem. Co.) was added to 1 mM. After 2 hrs the cells were harvested by centrifugation, washed once in BB buffer containing 0.5 mM phenylmethylsulfonylfluoride. Cells were ruptured by sonication (Branson Sonifier 350) with 3 bursts of power for 30 sec each with intermittent cooling in ice water. The broken cell suspension was cleared by centrifugation (15,000 rpm for 20 min, Sorvall SS34) and the supernatant was discarded. The pellet was resuspended in 10 ml BB buffer containing 6 M guanidine-HCl and allowed to stand overnight on ice. Insoluble debris was removed by centrifugation and the supernatant (Fraction I) was then loaded onto nitrilotriacetic acid agarose (NTA-agarose, Qiagen, Inc., Chatsworth, Calif.), and immobilized metal affinity column, charged with Ni2+ and equilibrated with BB buffer. The column (1.5 ml) was washed with BB buffer, then eluted stepwise with increasing concentrations of imidazole (60 mM, then 100 mM). REC2 protein eluted with 100 mM imidazole. Fractions (1 ml) were collected and those containing REC2 protein (5 ml) were pooled and dialyzed against TNE buffer (50 mM Tris-HCl, pH 8.5, 100 mM NaCl, 1 mM EDTA) containing 6 M urea. After 3 hrs, the dialysis bag was placed in a small beaker and covered with 10 ml of the same buffer. TNE buffer without urea (10 ml) was then added every 15 min until the volume was 200 ml. Failure to remove denaturant by this slow dialysis regimen resulted in precipitation of the REC2 protein. This sample (Fraction II) was then loaded on a heparin-agarose column (1 ml), followed by a wash (5 ml) with TNE buffer. REC2 protein was eluted with TNE buffer plus 0.25 M NaCl and fractions of 0.5 ml were collected. REC2 eluted at tubes 7–9. The pooled peak was dialyzed against TNE buffer containing 10% glycerol, aliquoted, and stored frozen at −70°. The molar extinction coefficient calculated for REC2 protein at 280 nm was $3.16 \times 10^4$ $M^{-1}$ $cm^{-1}$.

6.4. The Activity of Recombinant REC2

The activity of the recombinant Rec2 protein was determined in three different assays. In each of these assays recombinant Rec2 displayed the same qualitative characteristics that had been observed in the study of the Rec2 fragment obtained from Ustilago.

6.4.1. Materials and Methods

Oligonucleotides

Oligonucleotides were synthesized on an Applied Biosystems 394 nucleic acid synthesizer and purified by capillary electrophoresis. Concentrations were determined spectrophotometrically as total nucleotide using $\epsilon_{260} = 8.3 \times 10^3$ $M^{-1}$ $cm^{-1}$. Oligonucleotides were labeled with $^{32}P$ using polynucleotide kinase and [τ-$^{32}P$]ATP according to van de Sande, J. H., et al., 1973, BIOCHEM. 12: 5058. Specific activities of oligonucleotides were 1.5–2.5×10³ cpm per fmol (as molecules). Hybrid duplexes were prepared by annealing the appropriate complementary oligonucleotides in stoichiometric amounts at 65° C. in 0.4 M NaCl for 15 min, then purified and freed of any excess single-stranded oligonucleotide by electrophoresis in D600 gel (AT Biochem, Malvern, Pa.). The duplex oligonucleotide was excised in a band from the gel, then electroeluted and concentrated after precipitation with ethanol.

Hairpins

DNA 5'TAGAGGATCCCCGGGTTTTCCCGGG-GATCCTCTAGAGTTTTCTC3' (SEQ ID NO:4)
DNA/RNA chimera 5'TAGAGGATCCCCGGGTTTTC-CCGGGGAUCCUCUAGAGTTTTCTC3' (SEQ ID NO:5)

Duplexes 72-mer 5'TTACGAATTCGAGCTCGGTACCCGGG-GATCCTCTAGAGTCGACCTGCAGGCATG-CAAGCTTGGCACTGGCCG3' (SEQ ID NO:6)
3'AATGCTTAAGCTCGAGCCATGGGC-CCCTAGGAGATCTCAGCTGGACGTCCG-TACGTTCG AACCGTGACCGGC5' (SEQ ID NO:7)
50-mer 5'TTACGAATTCGAGCTCGGTACCCGGG-GATCCTCTAGAGTCGACCTGCAGG3' (SEQ ID NO:8)
3'AATGCTTAAGCTCGAGCCATGGGC-CCCTAGGAGATCTCAGCTGGACGTCC5' (SEQ ID NO:9)
30-mer 5'TTACGAATTCGAGCTCGGTACCCGGG-GATC3' (SEQ ID NO:10)
3'AATGCTTAAGCTCGAGCCATGGGCCCCTAG5' (SEQ ID NO:11) or RNA 30-mer
3'AAUGCUUAAGCUCGAGCCAUGGGCCCCUAG5' (SEQ ID NO:12)

Reactions

Joint molecule formation was measured by a filter retention assay in which complexes comprised of single-stranded and duplex DNA molecules were trapped on nitrocellulose filters. The assay was developed by Bianchi, M., et al., 1983, CELL 34: 931, to measure metastable intermediates that may not survive removal of protein. Samples (20 µl) were withdrawn into 1 ml of 10× SSC (SSC is 0.15 M NaCl, 0.015 M Na citrate, pH 7.8) without deproteinization and the mixture passed on to a nitrocellulose filter (BA85, 0.45µ filter, Schleicher & Schuell, Keene, N.H.) that had been soaked extensively in water followed by a rinse in 10× SSC. Filters were washed twice with 1 ml of 10× SSC, then dried under a heat lamp, and the bound radioactive DNA quantitated by scintillation counting in Econofluor (Dupont NEN).

Identical strand pairing reactions were carried out essentially the same as the described by Rao, B. J., and Radding, C. M., 1993, PROC.NATL.ACAD.SCI. 90: 6646, except that the carrier DNA used was polyd[A-T] rather than heterologous single stranded oligonucleotide. Reactions contained M13 single stranded circular DNA, and $^{32}P$-labeled oligonucleotide. The identical strand oligonucleotide was a 33-mer 5'ACAGCACCAGATTCAGCAAT-TAAGCTCTAAGCC3' (SEQ ID NO:13) which corresponds to residues 207–239 of M13 DNA (van Wezenbeek, P. M. G. F., et al., 1980, GENE 11: 129). Control reactions measuring hybrid DNA formation between complementary antiparallel sequences utilized M13mp18 DNA and $^{32}P$-labeled 44-mer 5'GAATTCGAGCTCGGTACCCGGGGATC-CTCTAGAGTCGACCTGCA3' (SEQ ID NO:14) which corresponds to residues 412–455 of M13mp18 DNA.

Renaturation reactions were carried out by monitoring the increase in resistance of denatured P22 [$^3H$] DNA to digestion by S1 nuclease as described before (Kmiec, E. J., and Holloman, W. H., 1994, EUR.J.BIOCHEM. 219: 865). ATPase activity was measured in reactions (per 50 µl) containing 25 mM Tris-HCl, pH7.5, 10 mM MgCl$_2$, 1 mM DTT, 20 µM M13 DNA, 0.5 mM [τ$_{-32}$P]ATP at 10⁵ cpm per nmol. Reactions were started by addition of REC2 protein, conducted at 37°, and quenched by addition of 100 µl 10 mM potassium phosphate, 100 µl acetone, 50 µl ammonium molybdate in 4 N H$_2$SO$_4$, 700 µl isobutanol:benzene (1:1). After the mixture was vortexed and the phases separated, half (350 µl) of the organic phase (top) was removed and the radioCerivity determined by Cerenkov counting.

Renaturation reactions (40 µl) were performed using 20 µM denatured P22 [$^3H$] DNA (as nucleotide) either in the presence of 1 mM ATP or with no ATP. Reaction were carried out at 37° for 30 min. DNA renatured indicates the level of input DNA that became resistant to digestion by S1 nuclease. In general only 80–85% of the DNA could be converted to a form resistant to S1 hydrolysis. The data presented are uncorrected for this value. Protein independent renaturation was <5%.

ATPase reactions were performed as described above in the presence or absence of 20 µM M13 DNA (as nucleotide) at 37° for 15 min.

Identical strand pairing reactions were carried out in a total volume of 200 μl which contained 25 mM Tris acetate, pH 7.5, 10 MM $Mg^{2+}$ acetate, 1 mM dithiothreitol, 1 mM ATP, 100 μg/ml bovine serum albumin, 10 μM polyd[A–T] (as nucleotide), 0.41 nM M13 single stranded circular DNA (as molecules), and 0.85 nM 32P-labeled identical strand 33-mer oligonucleotide (as molecules). Reactions were initiated by addition of REC2 protein to 0.5 μM, incubated at 37°, and samples (20 μl) removed. Reactions were then stopped by addition of 200 μl reaction buffer minus DNA and the mixture immediately centrifuged through Ultrafree-MC cellulose filters (Millipore) at 2000×g for 6 min in a table top centrifuge. Filters were washed with an additional 100 μm of buffer, centrifuged for 3 min and the radioactivity bound then determined. In the absence of M13 single-stranded DNA the background of $^{32}P$ label retained was usually 5% of the input labeled oligonucleotide. Results are corrected for this background.

Complementary strand pairing reactions were carried out using M13mp18 DNA and complementary antiparallel sequence oligonucleotide 44-mer (200 μl) utilized 0.47 nM M13mp18 DNA and 1.14 nM $^{32}P$-labeled 44-mer and were processed as above.

Formation of DNA/DNA and DNA/RNA hybrids were formed as follows. DNA/DNA duplex fragments were prepared by annealing two complementary $^{32}P$-labeled oligonucleotides of the indicated lengths and purified as described by gel electrophoresis. The sequences utilized spanned the multiple cloning site of M13mp19 DNA. Pairing reactions contained 25 mM Tris-HCl, pH 7.5, 10 mM $MgCl_2$, 1 mM ATP, 1 mM dithiothreitol, 0.3 nM M13mp19 single-stranded circular DNA (as molecules), 0.23 nM duplex $^{32}P$ DNA fragment (as molecules) and 0.25 μM REC2 protein. At the appropriate time aliquots were removed and joint molecules then determined. RNA/DNA duplexes fragments were prepared by hybridizing either complementary sequence DNA oligonucleotides or else complementary RNA and DNA oligonucleotides were tested for pairing. In this latter case the RNA strand was complementary to the M13mp19 multiple cloning region. In both cases only the (+) DNA strand oligonucleotides were radiolabelled.

Joint molecule formation with chimeric hairpin duplex oligonucleotides were performed as follows. Self-complementary DNA or mixed DNA-RNA chimeric oligonucleotide 44-mer sequences were synthesized on an Applied Biosystems 394 DNA/RNA synthesizer. After labeling at the open 5'-OH with [γ-$^{32}p$]ATP and polynucleotide kinase the hairpin was sealed with DNA ligase. Homologous pairing with an RNA/DNA oligonucleotide hairpin. Joint molecule formation was performed as described above in reactions containing 25 mM Tris-HCl, pH 7.5, 10 mM $MgCl_2$, 1 mM ATP, 1 mM dithiothreitol, 0.45 nM M13mp18 or M13mp19 DNA (as molecules), 1.1 nM $^{32}P$-labeled oligonucleotide, and 0.5 μm REC2 protein. Aliquots (20 μl) were removed to 1 ml of 10× SSC and joint molecule formation was measured after washing onto nitrocellulose filters.

6.4.2. Results

6.4.2.1. Expression of the Recombinant REC2 Protein

As described in section 6.3, a 2.5 kbp genomic DNA fragment with the REC2 open reading frame engineered to contain an NdeI site at the initiation methionine codon was inserted behind the φ10 bacteriophage T7 promoter in the pET vector system which is designed for over-expression of genes in E. coli. (Studier, F. W., and Moffatt, B. A., 1986, J.MOL.BIOL. 189: 113). After induction with IPTG, a protein with a mass of ≈110 kDa accumulated in the cells as determined by SDS-gel electrophoresis. In a control in which cells contained the vector without the REC2 gene, no accumulation of the 110 kDa protein was noted. With the use of antiserum obtained from rabbit immunized with a 12 kDa fusion protein containing 96 amino acid residues from the carboxy terminus of the REC2 protein, it was determined that the 110 kDa protein cross-reacted. While the bulk of the overexpressed protein was insoluble, a small fraction (≈5%) remained soluble even in low ionic strength buffer. This soluble 110 kDa protein was purified with the aid of the antiserum as a REC2-specific reagent following chromatography on heparin agarose and fast protein liquid chromatography (FPLC) separation on a Pharmacia MonoS column. N-terminal amino acid sequence determination of 15 residues confirmed the identity of the 110 kDa protein as REC2. Since the predicted mass of REC2 is only 84 kDa, it is concluded that the protein runs anomalously under conditions of SDS-gel electrophoresis.

To enable purification of the protein a 2.5 kbp DNA fragment containing the REC2 gene was inserted into pET14b, which was designed for expression of fusion proteins preceded by a hexa-histidine leader sequence. Due to the utility of the histidine-leader sequence in affinity chromatography, the hexa-histidine-REC2 fusion was considered more amenable for biochemical studies. After induction of cells with IPTG the insoluble fraction containing the bulk of the REC2 protein was collected and dissolved in guanidine-HCl (Fraction 1). REC2 protein was then isolated using immobilized metal affinity chromatography. The denatured protein bound stably to a $Ni^{2+}$-NTA column and contaminating proteins which lacked the histidine leader were removed by extensive washing. Inclusion of 0.5 M salt in the buffer reduced nonspecific ionic interaction of contaminating proteins. REC2 protein was eluted with an increasing gradient of imidazole, then renatured after exchanging the guanidine-HCl for urea, followed by gradual stepwise removal of urea. The resulting fraction containing highly purified REC2 protein was completely soluble (Fraction II) and was further purified by chromatography on heparin-agarose (Fraction M). Protein in the final fraction was comprised largely of the 110 kDa REC2 protein although a few other lower molecular weight proteins were evident upon close inspection. It was considered that these were likely to be proteolytic degradation products since (i.) no such protein bands were evident in similarly processed preparations of extracts made from cells not overexpressing REC2 and (ii.) the level of these protein bands increased with a concomitant decrease in the 110 kDa band as a result of prolonged handling of cell extracts in the initial processing (not shown).

6.4.2.2. Reannealing of Complementary Strands of DNA

Figure 3B:
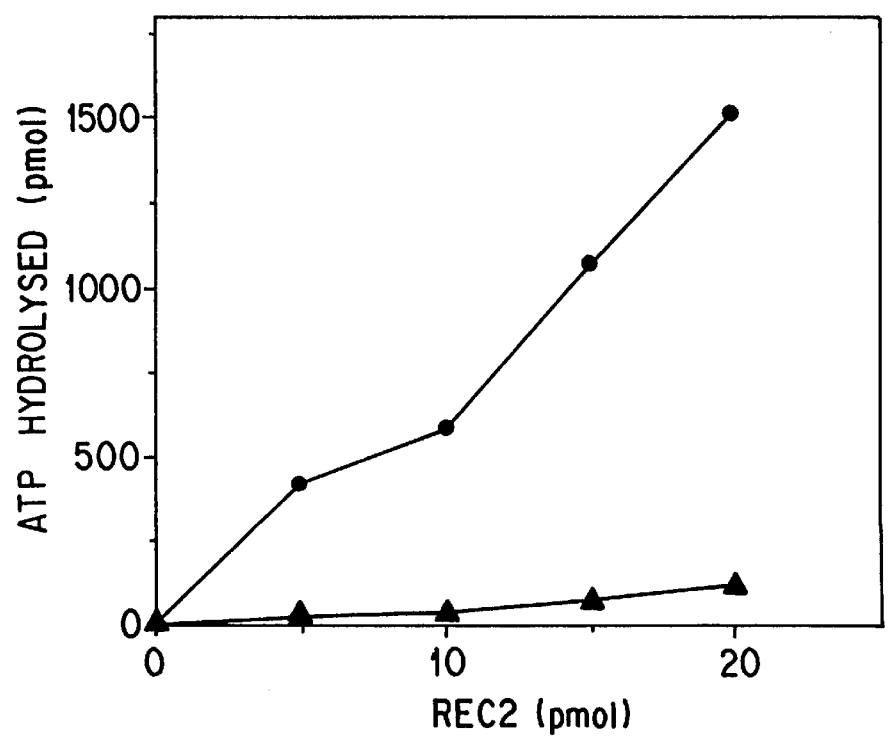

The purified Rec2 protein promoted the reannealing of complementary single strands of P22 viral DNA, in an ATP dependent manner, and catalyzed a DNA-dependent ATP hydrolysis. See FIG. 3A and 3B. The turnover number for the ATP hydrolytic reaction was calculated as 5.3/minute, which is below the 225/minute rate calculated in kinetic studies on the 70 kDa fragment of Rec2 obtained from Ustilago extracts.

6.4.2.3. Reannealing of a 33-Mer to Single Stranded, Circular DNA

Figure 4A:
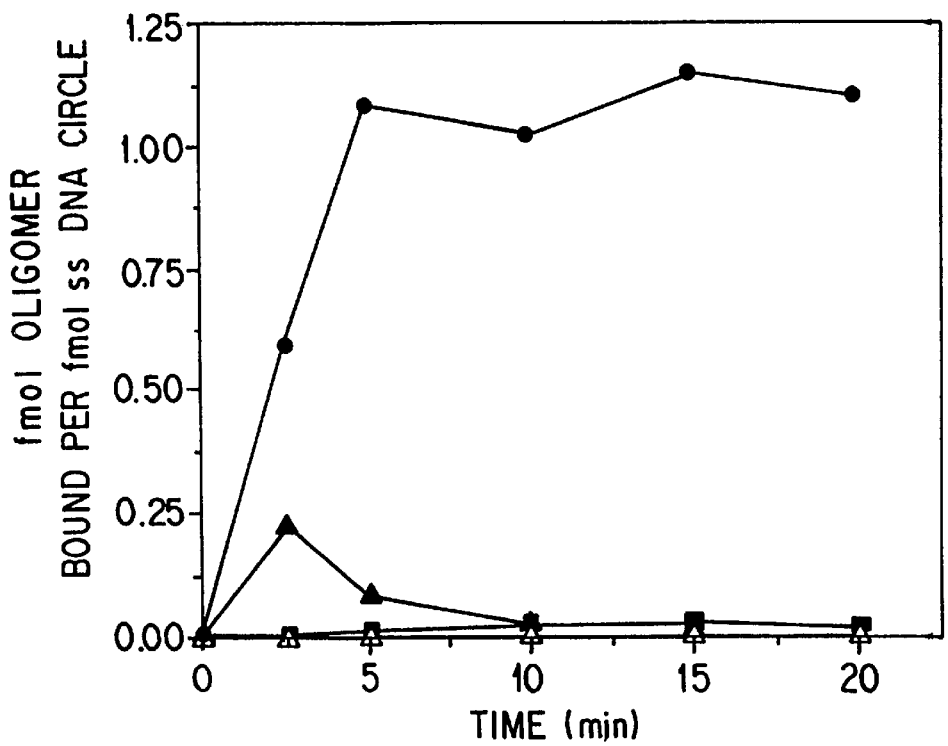
FIGS. 4A and 4B. Complementary and identical strand pairing by recombinant REC2 with circular single stranded M13.

Homologous pairing activity of the REC2 protein was demonstrated using an assay that is free from interference by reaction leading to heteroduplex formation that can occur through simple second-order renaturation of complementary single strands of DNA (for review see Kmiec, E. B., and Holloman, W. K., 1994, J.BIOL.CHEM. 269: 10163). This assay measures identical sequence recognition and was first reported for RecA protein by Rao, B. J., and Radding, C. M., 1993, PROC.NATL.ACAD.SCI. 90: 6646. An oligonucleotide (33-mer) of identical sequence and polarity as residues 207–251 of bacteriophage Mi 3 was synthesized and labeled with $^{32}$P at the 5'-end. When this identical sequence oligonucleotide was present in a reaction at a two-fold molar excess over M 13 single stranded circles, REC2 protein promoted formation of a specific complex between the oligonucleotide and M13 DNA that could be trapped on a membrane filter. The complex that formed was completely dependent on ATP (FIG. 4A) and was composed of almost exactly one mole of oligonucleotide per mole of M13 DNA as molecules. No stable complex formed when M13 DNA was replaced by φX174 single-stranded circles or when ADP was included in the reaction. The complex was completely dissociated by addition of proteinase K.

Figure 4B:
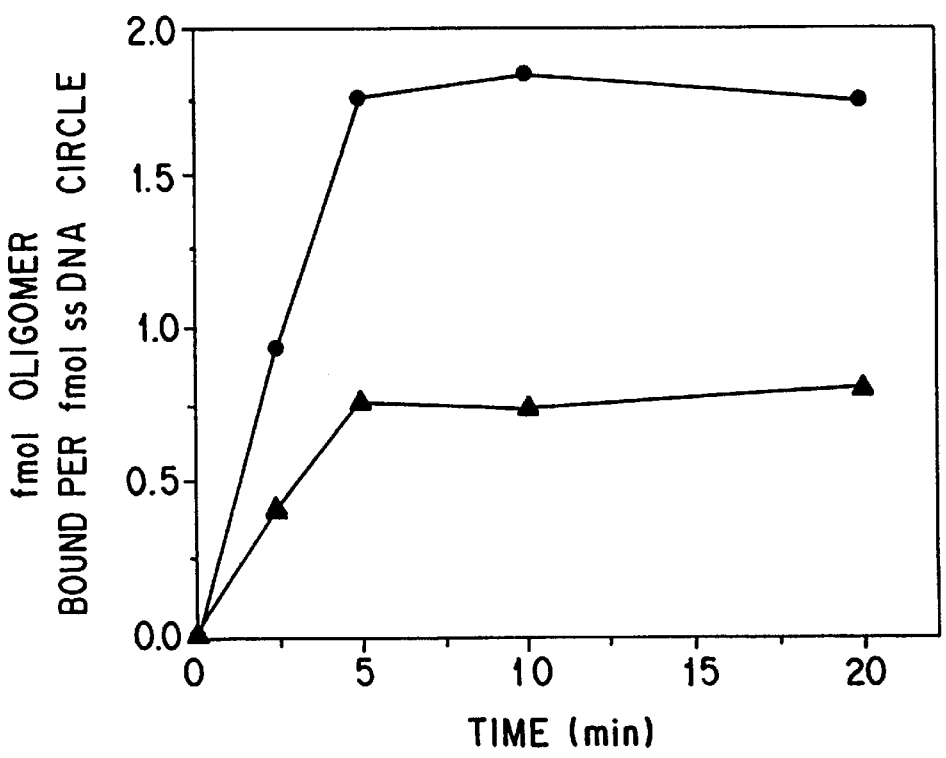

In a control reaction using an oligonucleotide complementary and anti parallel to M13 sequence, stable complexes were also formed (FIG. 4B). Interestingly, the stoichiometry of DNAs in the complex was approximately 2 moles of oligonucleotide per mole of M13 single stranded circles. After treatment with Proteinase K the ratio dropped to approximately I to I as would be expected for formation of a heteroduplex joint stabilized through Watson-Crick base pairing.

6.4.2.4. Size Dependence of Duplex Formation

Figure 5A:
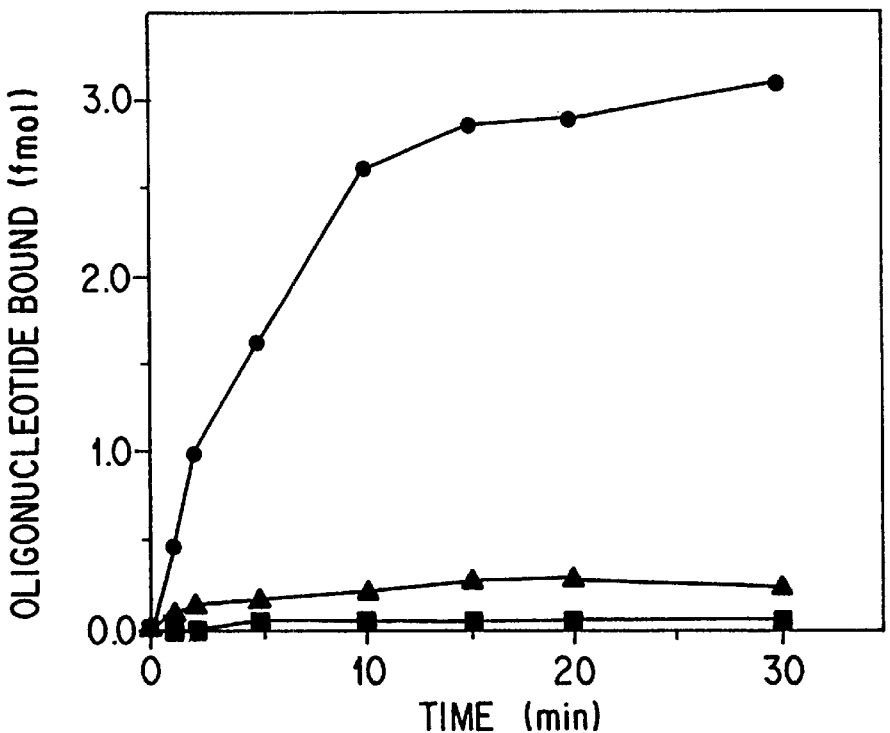
FIGS. 5A and 5B. Threshold length dependence for pairing with DNA/DNA and DNA/RNA hybrids.

A series of duplex DNA oligonucleotides of defined lengths was tested for activity in joint molecule formation in a study aimed at exploring the minimum length requirement for homologous pairing by REC2 protein. Joint molecule formation was monitored in reactions containing radiolabelled duplex DNA and homologous single-stranded circular M13 DNA. Joint molecules were assayed by measuring retention of labeled DNA on nitrocellulose filters. In reactions containing a duplex 70-mer, there was efficient joint molecule formation, but when a 50-mer was used the level dropped markedly (FIG. 5A). No joint molecules could be detected when the duplex was 30 bp in length. Thus, in the case of REC2 there is a minimum length requirement for joint molecule formation that is between 5 and 7 turns of duplex, well above that necessary for stabilizing DNA in the double-stranded conformation Thomas, C. A., 1966, PROG.NUC.ACID RES.MOL.BIOL. 5:315.

Figure 5B:
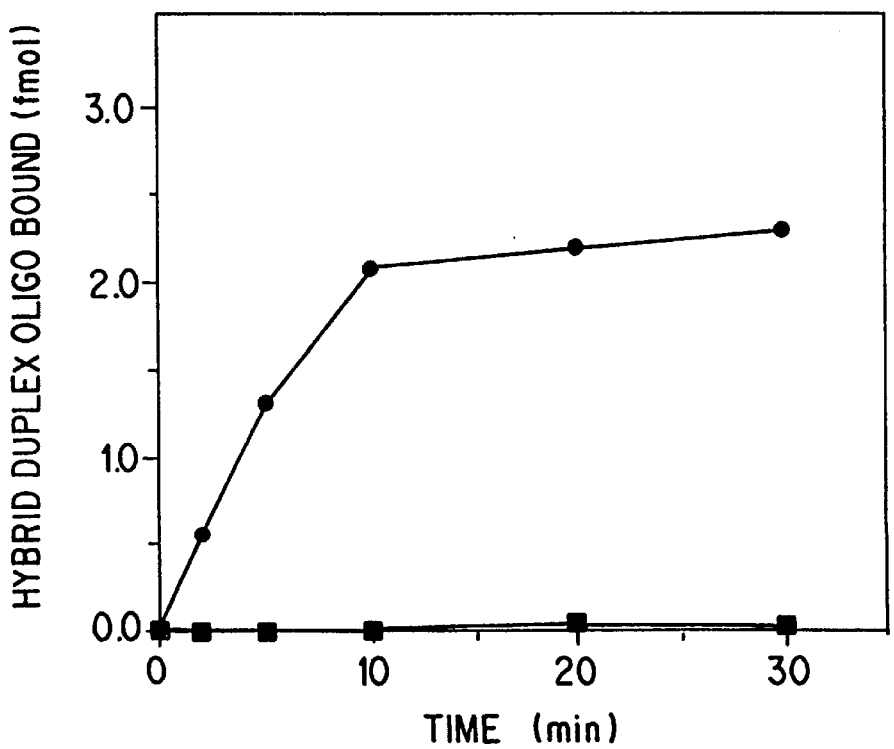

When the 30-mer was composed of an RNA/DNA hybrid there was considerable joint molecule formation (FIG. 5B). The polarity of the RNA directed the reaction. Complexes were formed when the RNA sequence was complementary to the M13 DNA sequence, but not when it was identical.

Activity of Hairpin Duplexes in Joint Molecule Formation

Figure 6:
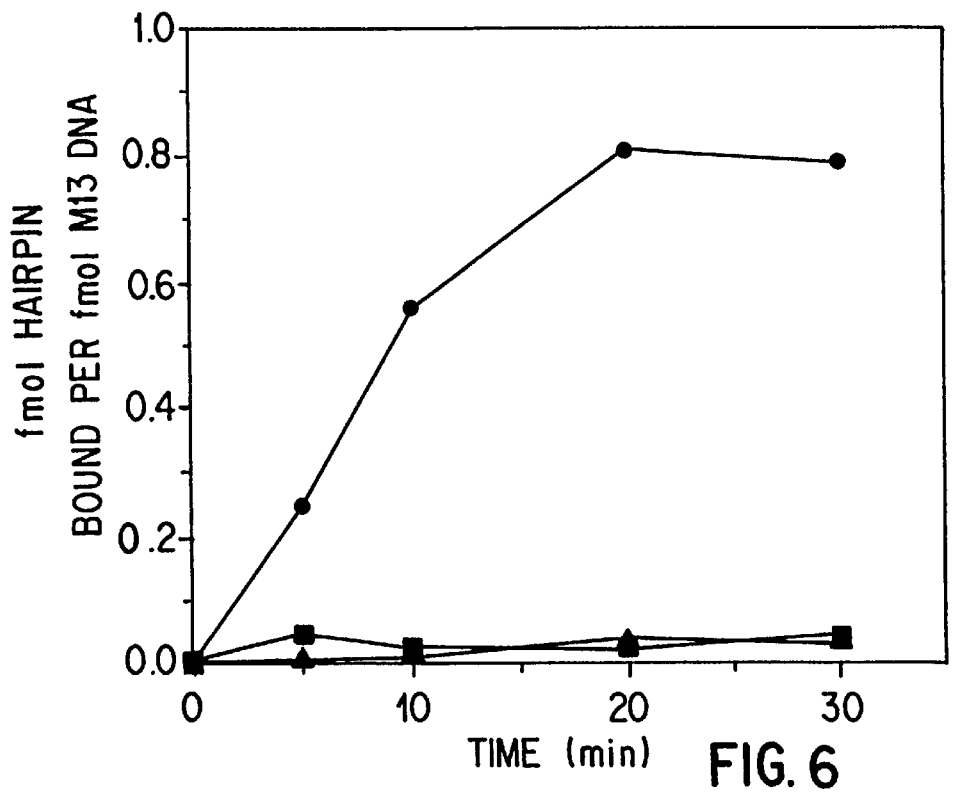
FIG. 6. Homologous pairing with an RNA/DNA oligonucleotide hairpin. (circles) RNA/DNA chimeric hairpin with M13mp19 DNA; (triangles) RNA/DNA chimeric hairpin with M13mp18 DNA; (squares) DNA hairpin with M13mp19 DNA. p FIG. 7. Contribution of RNA to homologous pairing of chimeric hairpin duplexes. Hairpin forming chimeric RNA-DNA oligonucleotide 44-mers were synthesized such that the RNA length was progressively reduced by replacement with DNA residues. The total base-pair-forming length along both strands was kept at 18 residues.

When the substrates in pairing reactions include linear duplex molecules and single stranded circular DNA, interpretation of pairing data can be complicated by the contribution of complementary strand hybridization to said exchange (Kmiec, E. B. and Holloman, W. K., 1994, J.BIOL.CHEM. 269: 10163). To study the influence of RNA on the homologous pairing aspect of the reaction in isolation without complication from the strand exchange aspect, a duplex substrate was devised that could serve as a reactant for homologous pairing but which would be topologically barred from proceeding past that phase on the reaction pathway. This was a linear heteroduplex of RNA and DNA with hairpin caps on both ends (FIG. 6A). It was prepared by synthesis of a single 44-mer oligonucleotide which contained an inverted repeat of complementary sequences. The sequence was designed so that intramolecular association of complementary sequences would result in formation of a linear duplex with hairpin ends. There was a total of 18 base pairs in the duplex region. Along one strand was a stretch of 18 residues composed entirely of DNA nucleotides. Along the other strand were the 18 complementary residues, 15 of which in contiguous array were RNA nucleotides. At the ends were caps of 4 residues each of oligo dT connecting the complementary strands. The hairpin molecule was labeled at the single open 5'-end with [γ-32P]ATP and polynucleotide kinase, then sealed with DNA ligase, yielding a covalently closed linear duplex. Homologous pairing with single stranded circular DNA as catalyzed by REC2 protein was highly efficient reaching almost 1 molecule of hairpin duplex (see FIG. 6B) per molecule of single-stranded circular DNA.

Figure 7:
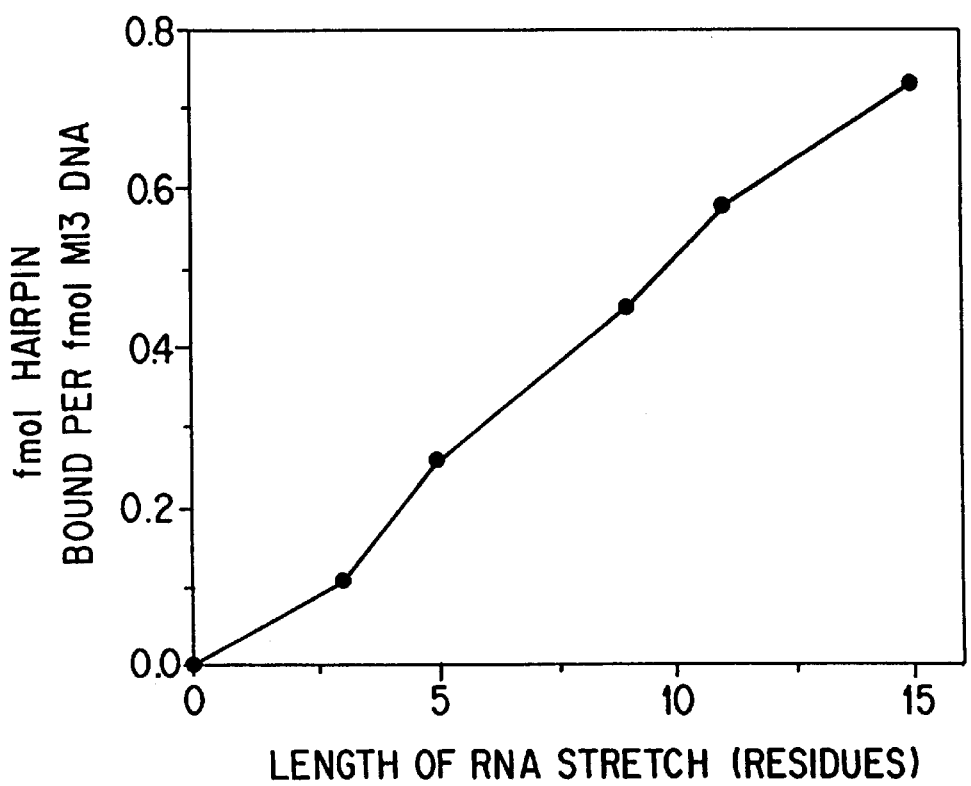

When the length of the RNA stretch was reduced by systematic replacement of the ribonucleotide residues with deoxyribonucleotide counterparts, the pairing efficiency decreased but did not drop to zero even when only 3 RNA residues remained (FIG. 7). When all of the nucleotides residues present were deoxyribonucleotides there was no reaction. Thus, addition of RNA to a duplex can activate it for pairing under conditions where a completely DNA duplex is inactive. Furthermore, addition of RNA to a duplex brings the minimum homology threshold required for REC2-catalyzed pairing in line with the minimum threshold of length necessary for duplex stability.

6.5. The Use of Recombinant REC2 to Promote Homologous Recombination

Figure 8:
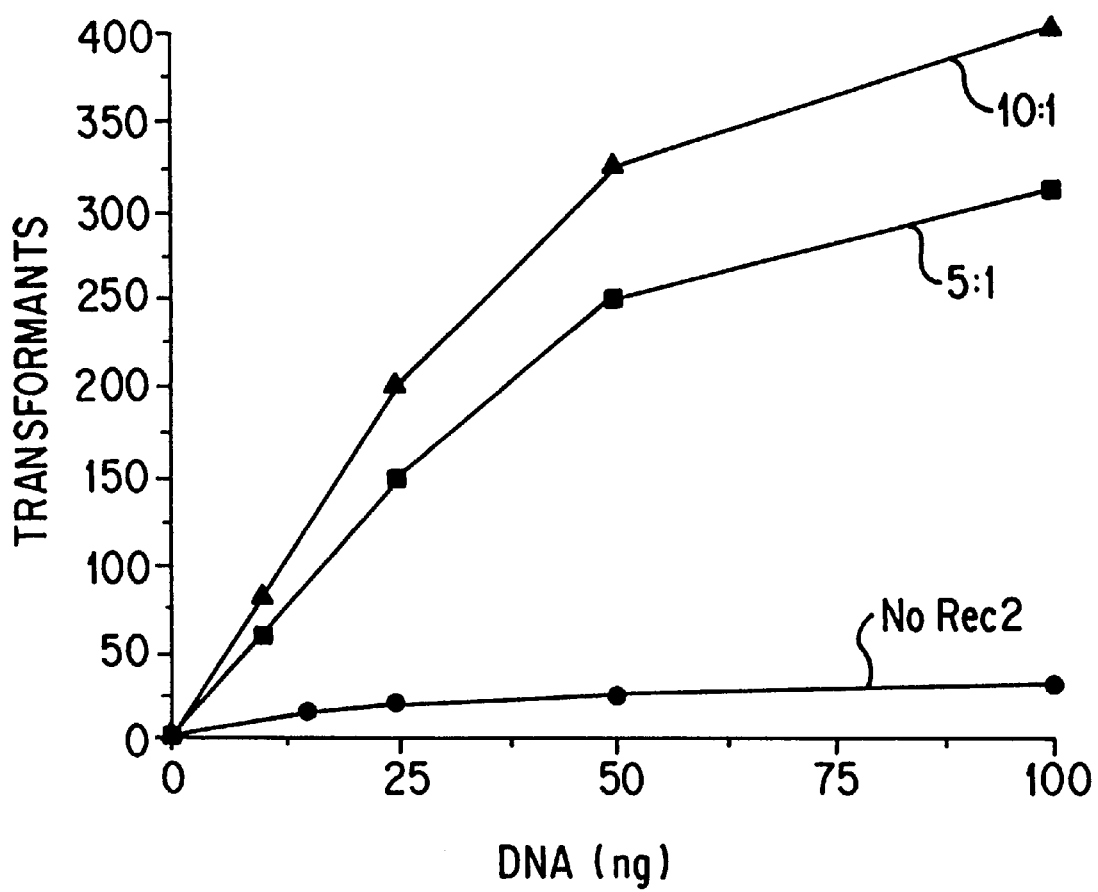
FIG. 8. Transformation of Saccharomyces strain B7528 by homologous recombination of a 50-mer ssDNA oligomer containing a one base insertion. (-X-), 10:1 mol recombinant Rec2:mol oligomer; (-■-), 5:1.

The purified Recombinant Rec2 was used to promote homologous recombination in the iso-1-cytochrome c mutant Saccharomyces system developed by Moerschell, R. P. et al., 1988, PROC.NATL.ACAD.SCI. 85: 524. Briefly, a frame shift mutation caused by the deletion of one nucleotide prevents the growth of mutant strain on low grade carbon sources. A ssDNA 50-mer containing the wild type sequence extending from 14 bp 5' of the deletion to 36 bp 3' of it is complexed with recombinant Rec2, dialyzed into 2 mM Tris HCl (pH=7.5) by incubation at 31 C. for 10 minutes at a concentration of 20 ng ssDNA/µl. The Rec2 protein was present in 5 and 10 fold molar excess. Thereafter the complex is mixed with $10^6$ mutant Saccharomyces in a final volume of 25 µl, incubated on ice for 20 minutes and electroporated into the cells. The results presented in FIG. 8 indicate that the presence of Rec2 at a protein:oligonucleotide molar ratio of 5:1 cause an approximately 10 fold increase in the rate of wild type transformants. In the linear portion of the dose-response curve the rate without Rec2 was 0.6 transformants per $10^6$ cells per ng DNA; with a 10× molar ratio of Rec2 present the rate increased to 8.4 transformants per $10^6$ cells per ng DNA.

6.6. The Use of REC2 $(T \rightarrow A)^{697}$ Expression Vector to Promote Homologous Recombination in Ustilago

6.6.1. Construction of the $(T \rightarrow A)^{697}$ Expression Vector

Site directed mutations were introduced into the REC2 gene by the method of Ho, S. N., et al., 1989, GENE 77: 51–59. Briefly, a first PCR reaction generates two REC2 gene fragments having overlapping ends that contain the desired mutation. The fragments are denatured and reannealed together. Heteroduplexes are formed by pairing at the 3' ends, which can then be extended to yield a fully duplex fragment that spans the combined sequence of the two PCR fragments. In a second round of PCR, this spanning fragment is amplified, cloned and thereafter inserted into the REC2 gene. Using this technique the Thr codon (ACG) at position 697 was mutated to an Ala codon (GCG), this gene is termed REC2–10 hereinafter.

6.6.2. Results Showing the Rate of Homologous Recombination

To test the activity of REC2–10 the plasmid pCM441/REC2 and pCM441/REC2–10 were constructed that lack a Ustilago replication origin and contains a 3.2 kb fragment spanning the REC2 and REC2–10 genes, respectively and a modified ADE1 gene of *U. maydis*, on a 5.0 kbp BamHI-XbaI fragment that was isolated by complementing the adenine auxotrophy of the ade1-1 mutant. The ADE-1 gene was modified by removing an essential 100 bp NcoI fragment from within the coding region of the gene. The NcoI created gap within the ADE1 gene does not overlap the ade1-1 lesion, yet enables transformation of ade1-1 strains to adenine prototrophy upon a recombination of the ade1-1 gene and the circular pCM441 plasmid at a site between the ade1-1 lesion and the NcoI deletion. The experimental system is described in greater detail in Rubin, B. P. et al., 1994, MOL.CELL.BIOL. 14: 6287–96, which is hereby incorporated by reference in its entirety.

The results of transformation with either pCM441/REC2 and pCM441/REC2–10 of wild-type Ustilago and of the rec2–1 strain lacking a functional Rec2 are shown below.

TABLE I

| Plasmid | Transformants per 5 µg | |
|---|---|---|
| | rec2-1 | w.t. |
| pCM441 | 1 | 76 |
| pCM441/REC2 | 83 | 90 |
| pCM441/REC2-10 | 720 | 665 |

These data show that the REC2-10 gene can cause a rate of homologous recombination in a wild type eukaryotic cell 8–10 fold greater than that of the wild type cell. Bacteria carrying the plasmid pCM441/REC2–10 were deposited in the ATCC on Jan. 10, 1995 as accession No. 69740 with the designation BCM677.

6.7. The Construction of a REC2 Vector for Expression in Mammalian Cells

The REC2 mammalian expression vector utilizing the CMV promoter and the poly A region of bovine growth hormone was constructed as follows. A 130 bp fragment of the 5' region of ustilago REC2 was PCR amplified by two primers. The 5' primer contained a Bam HI cloning site and CACC sequence prior to the AUG codon for efficient translation. The 3' primer contained a region spanning a unique MunI restriction site in Ustilago REC2 sequence. The PCR amplified fragment was digested by BamH1 and MunI restriction enzymes and gel purified. A mammalian expression vector pCDNA3 was digested by BamH1 and XhoI restriction enzymes. Also, the 2.9 kb fragment containing Ustilago REC2 was isolated by MunI and BamH1 digestion of pET14 REC2 vector. These three purified fragments, 130 bp of PCR amplified region of the REC2, 2.9 kb of REC2 sequence, and 5.4 kb of pCDNA3 were ligated together at equal molar ratios and the ligation mixture was transformed into DH5a competent cells. Several clones were sequenced and shown to have a correct sequence within the 130 bp PCR amplified region. This vector also contained a neomycin resistance gene expressed from SV40 early promoter enabling selection of permanent clones by G418 resistance. Bacteria carrying the resultant plasmid pCMV-REC2 were deposited in the ATCC on Jan. 5, 1995 as accession No. 69738.

We claim:

1. A method of promoting an alteration at a genetic locus of interest which comprises the steps of:
   a) introducing into a eukaryotic cell a nucleic acid which comprises a segment that is homologous with the locus of interest; and
   b) introducing into the eukaryotic cell a polydeoxynucleic acid expression vector that comprises a coding portion that encodes a protein that:
      (1) is an ATPase;
      (2) catalyzes the formation of complementary or identical strand pairings of polydeoxynucleic acids; and
      (3) promotes homologous recombination in a eukaryote;
      (4) wherein the normalized alignment score of the protein, compared to SEQ ID NO: 2, is at least about 150; and
      (5) wherein the coding portion hybridizes to the 2.8 Kb Bam HI REC2 insert of pCM346 when the coding portion is membrane immobilized and a final wash conditions is 40 mM $Na_2PO_4$, 1 mM EDTA, 1% SDS at 50° C.; and
   c) expressing the polydeoxynucleic acid expression vector in the cell so as to produce the encoded protein.

2. The method of claim 1, wherein the coding portion encodes a naturally occurring Rec2 recombinase or a naturally occurring recombinase that has been modified to remove a $p34^{CDC2}$ kinase consensus phosphorylation site.

3. The method of claim 2, wherein the coding portion encodes a protein comprising a recombinase of an ascomycetes yeast form fungal cell.

4. The method of claim 2, wherein the coding portion encodes a protein comprising a recombinase of an ascomycetes yeast form fungal cell that has been modified by the deletion of a $p34^{CDC2}$ kinase consensus phosphorylation site.

5. The method of claim 2, wherein the coding portion encodes a protein comprising a recombinase of a fungus selected from the group of fungal genera consisting of Ustilago, Saccharomyces and Aspergillus.

6. The method of claim 2, wherein the coding portion encodes a protein comprising a recombinase of a fungus selected from the group of fungal genera consisting of Ustilago, Saccharomyces and Aspergillus, which protein has been modified by the deletion of a $p34^{CDC2}$ kinase consensus phosphorylation site.

* * * * *